United States Patent [19]
Wang et al.

[11] Patent Number: 5,696,157
[45] Date of Patent: Dec. 9, 1997

[54] SULFONATED DERIVATIVES OF 7-AMINOCOUMARIN

[75] Inventors: Hui-Ying Wang; Wai-Yee Leung; Fei Mao, all of Eugene, Oreg.

[73] Assignee: Molecular Probes, Inc., Eugene, Oreg.

[21] Appl. No.: 749,753

[22] Filed: Nov. 15, 1996

[51] Int. Cl.$^6$ .................. A61K 31/37; C07D 311/16; C07D 311/18
[52] U.S. Cl. .................. 514/457; 549/285; 549/288; 549/289
[58] Field of Search .................. 514/457; 549/285, 549/288, 289

[56] References Cited

U.S. PATENT DOCUMENTS

| | | | |
|---|---|---|---|
| 4,279,992 | 7/1981 | Boguslaski et al. | 435/7 |
| 4,473,693 | 9/1984 | Stewart | 546/100 |
| 4,711,955 | 12/1987 | Ward et al. | 536/29 |
| 4,956,480 | 9/1990 | Robinson | 549/288 |
| 4,997,928 | 3/1991 | Hobbs, Jr. | 536/27 |
| 5,047,519 | 9/1991 | Hobbs, Jr. et al. | 536/23 |
| 5,049,673 | 9/1991 | Tsien et al. | 546/107 |
| 5,171,534 | 12/1992 | Smith et al. | 422/82.05 |
| 5,196,306 | 3/1993 | Bobrow et al. | 435/7.9 |
| 5,332,666 | 7/1994 | Prober et al. | 435/91.5 |
| 5,405,975 | 4/1995 | Kuhn et al. | 549/347 |
| 5,453,517 | 9/1995 | Kuhn et al. | 549/227 |
| 5,514,710 | 5/1996 | Haugland et al. | 514/512 |
| 5,516,911 | 5/1996 | London et al. | 548/236 |

FOREIGN PATENT DOCUMENTS 0 608 737 A1 of 1994 European Pat. Off. .
3044128 A1 of 1982 Germany .
94/05688 of 1994 WIPO .

OTHER PUBLICATIONS

Angelides, et al., J. Biol. Chem., 258, pp. 11948–11957, (1983).
Abd–El–Hafez, et al., Egypt. J. Pharm. Sci., 35, 113 (1994).
Mandour, et al., Egypt. J. Pharm. Sci., 36, 71 (1995).
Merchant, et al., J. Indian Chem. Soc., 34, 35 (1957).
Jackson, Meth. Enzymol., 230, 250 (1994).
O'Shea, et al., Electrophoresis, 17, 681 (1996).
Wittung, et al., Nature, 368, 561 (1994).
Raju, et al. Am. J. Physiol., 256, C540–C548, (1989).
Hermanson, Bioconjugate Techniques, Academic Press (1996).
Haugland, Molecular Probes Handbook of Fluorescent Probes and Research Chemicals, Sets 1–7 (1992).
Brinkley, et al., Bioconjugate Chem., 3, 2–13 (1992).
Haugland, et al., Meth. Mol. Biol. 45, 205 (1995).
Besson, Hetrocycles, 34, No. 2. 273 (1992).

*Primary Examiner*—Ba K. Trinh
*Attorney, Agent, or Firm*—Allegra J. Helfenstein; Anton E. Skaugset

[57] ABSTRACT

The present invention describes 7-aminocoumarin dyes that are substituted one or more times at the 3-, 6- and/or 8-positions by a sulfonic acid or a salt of a sulfonic acid, said dyes being useful as fluorescent probes or in the preparation of enzyme substrates, caged probes, or adducts with reducing sugars. The dyes of the invention optionally possess a reactive group useful for preparing fluorescent conjugates, which conjugates and methods for their preparation are described herein.

27 Claims, 2 Drawing Sheets

SULFONATED DERIVATIVES OF 7-AMINOCOUMARIN

FIELD OF THE INVENTION

The invention relates to compounds useful for fluorescent labeling and detection. In particular, sulfonated aminocoumarins that are useful as fluorescent tracing agents and enzyme substrates, reactive derivatives of sulfonated aminocoumarins useful as labels, and their conjugates.

BACKGROUND

Fluorescent dyes are known to be particularly suitable for applications in which a highly sensitive detection reagent is desirable. Dyes that are able to preferentially label a specific ingredient or component in a sample enable the researcher to determine the presence, quantity or location of that specific ingredient or component. In addition, specific systems can be monitored with respect to their spatial and temporal distribution in diverse environments.

Coumarin derivatives have been widely used as fluorescent labels or tracers and to prepare fluorogenic substrates for enzymes, especially where a fluorophore having excitation in the ultraviolet and generally blue to blue-green fluorescent emission was desired. In particular, derivatives of 7-aminocoumarin (for example 3-carboxyalkyl derivatives of 7-amino-4-methylcoumarin, as described by Robinson, U.S. Pat. No. 4,956,480 and 7-amino-4-methylcoumarin) and 7-hydroxycoumarin (often called umbelliferone; for example U.S. Pat. No. 4,279,992 to Boguslaski et al. (1981)) have been widely used blue fluorophores for the preparation of reactive dyes, labels for biomolecules, and reporters for enzyme substrates. However, the conventional coumarin dyes used in biological systems possess certain disadvantages: Some derivatives are not particularly soluble in aqueous systems (i.e. biological systems), they do not possess sufficient photostability for extended use, their fluorescence is quenched upon conjugation, particularly to proteins and they have other disadvantageous properties that restrict their use as fluorescent probes.

Selected sulfonated derivatives of 7-aminocoumarin of the invention and their conjugates possess enhanced brightness and photostability, relative to the corresponding non-sulfonated aminocoumarin, as well as having enhanced aqueous solubilities, while still preserving a bright blue fluorescence emission. Additionally, the dyes of the invention possess advantages over nonsulfonated aminocoumarin dyes in their utility as fluorescent probes for membranes.

7-Aminocoumarins have been widely used as fluorescent labels for biological polymers. For example, Robinson in U.S. Pat. No. 4,956,480 to Robinson describes succinimidyl esters and acid chlorides of 7-amino-4-methylcoumarin-3-alkanoic acids and provides examples of their conjugation to proteins. Kocher et al. (EP 0 608 737 A1) describes reactive 7-aminocoumarins that are used as labels for nucleotides, oligonucleotides and nucleic acids. The aminocoumarins of Kocher et al. are not substituted by sulfonic acid groups. 7-Dimethylaminocoumarin-4-acetic acid, succinimidyl ester has been conjugated to scorpion toxins by Angelides et al. (J. BIOL. CHEM. 258, 11948 (1983)).

Nonsulfonated aminocoumarin derivatives in which the amine is modified by a reactive triazine have been used as brightening agents; for example 7-((4-chloro-6-diethylamino)-s-triazin-2-yl)amino-3-phenylcoumarin.

Various sulfonated coumarins have also been described in the chemical literature; however, none of these has been a 7-aminocoumarin that has been sulfonated at one or more of the 3-, 6- or 8-positions, as required by the present invention.

Abd-El-Hafez et al. (EGYPT. J. PHARM. SCI. 35, 113, (1994)) describes the reaction of 6-nitrocoumarin-3-sulfonyl chloride with a variety of amines to yield the corresponding 6-nitrocoumarin-3-sulfonamide derivatives, which were then tested against bacteria, yeast and fungus for antimicrobial activity. Mandour et al. (EGYPT. J. PHARM. SCI. 36, 71 (1995)) describes coumarin-6-sulfonyl chloride and 6-nitrocoumarin-3-sulfonyl chloride, their sulfonamide derivatives and finally the thiadiazole and selenadiazole derivatives therein, which were tested for antimicrobial and antiaflatoxigenic activity. None of the compounds described above were 7-aminocoumarins, and none of the compounds described were utilized for their fluorescent properties.

Harnisch et al. (DE 3044128 A1) describes sulfonated 7-hydroxycoumarins that are additionally substituted by a heterocyclic moiety that is also typically sulfonated. The dyes are described as useful as fluorescent dyes for cellulose and amide containing materials, for preparing "counterfeit proof" paper and as laser dyes. Sulfonated 7-hydroxycoumarins and 7-alkoxycoumarins have been described, for instance by Merchant et al. (J. INDIAN CHEM. SOC. 34, 35 (1957)). None of the compounds described were 7-aminocoumarins.

The preparation of substituted or unsubstituted 7-aminocoumarin-3-sulfonic acids, 7-aminocoumarin-6-sulfonic acids, 7-aminocoumarin-8-sulfonic acids or 7-aminocoumarin-3,6-disulfonic acids, their chemically reactive derivatives and their conjugates nor their advantages over nonsulfonated 7-aminocoumarins has not been previously described.

BRIEF DESCRIPTION OF THE DRAWINGS

FIG. 3: A comparison of relative fluorescence of goat-anti-mouse antibody conjugates of 7-amino-4-methylcoumarin-3-acetic acid, succinimidyl ester (△) and the 7-amino-4-methyl-6-sulfocoumarin-3-acetic acid, succinimidyl ester (Compound 2, ▲). Conjugate fluorescence is determined by measuring the fluorescence quantum yield of the conjugated dye relative to that of the free dye and multiplying by the number of fluorophores per protein (as in Example 22). The conjugates of Compound 2 exhibit enhanced fluorescence with respect to the conjugates of the non-sulfonated dye.

SUMMARY OF THE INVENTION AND DESCRIPTION OF THE PREFERRED EMBODIMENTS

Figure 1:
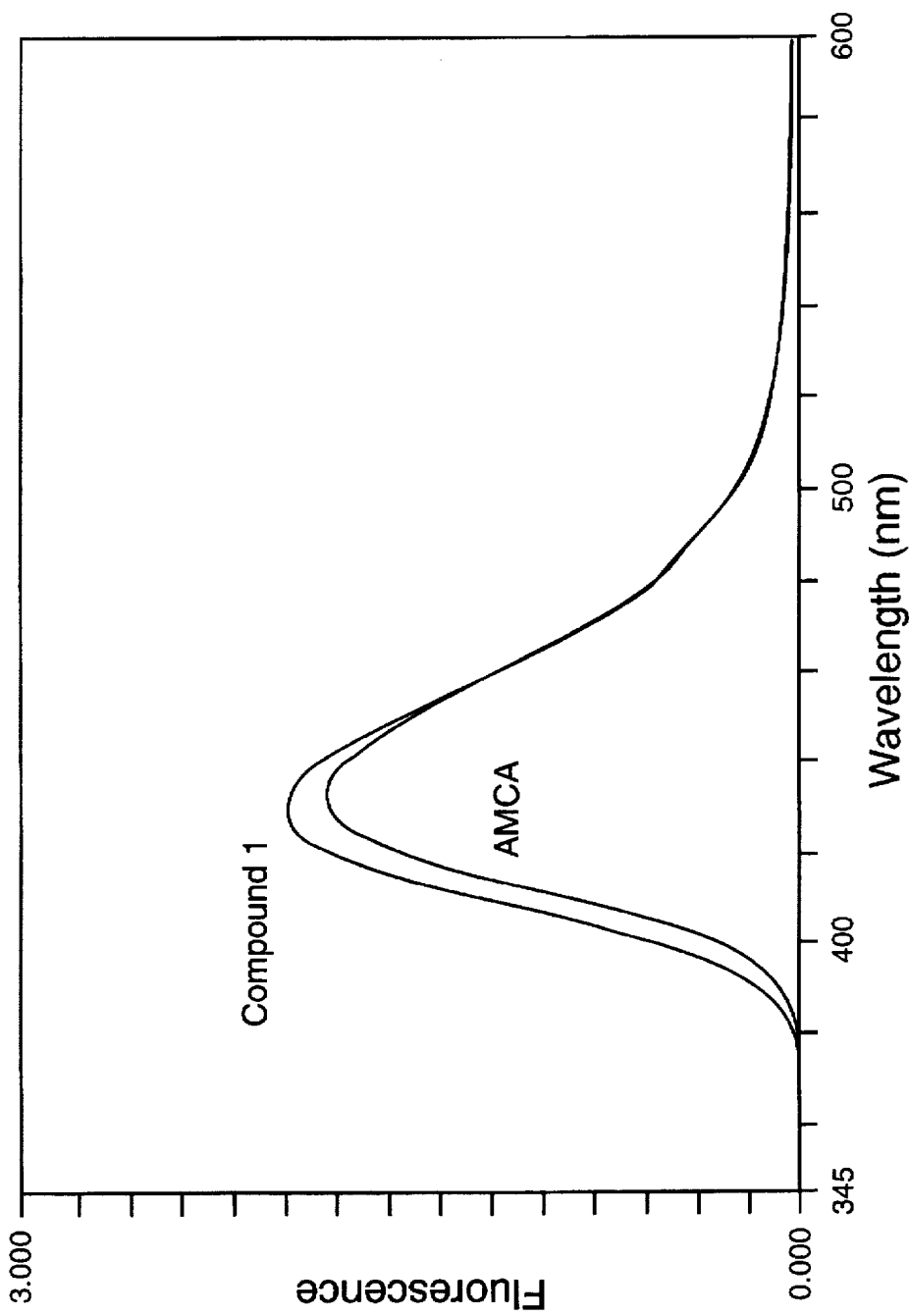
FIG. 1: A comparison of the fluorescence spectra in methanol of 7-amino-4-methylcoumarin-3-acetic acid (AMCA) and 7-amino-4-methyl-6-sulfocoumarin-3-acetic acid (Compound 1), recorded at equal dye concentrations. The fluorescence spectra of Compound 1 exhibits enhanced fluorescence relative to the non-sulfonated coumarin, with little shift in emission wavelength.

The present invention encompasses 7-aminocoumarin dyes that are substituted one or more times at the 3-, 6- and/or 8-positions by a sulfonic acid or a salt of a sulfonic acid that are useful as fluorescent probes or for preparation of enzyme substrates, caged probes, or adducts with reducing sugars. The dyes of the invention optionally possess a reactive group useful for preparing fluorescent conjugates, which conjugates and methods for their preparation are described herein.

The compounds of the invention are all 7-aminocoumarins substituted one or more times at the 3-, 6- and/or 8-positions by a sulfonic acid or salt of a sulfonic acid, $SO_3X$, where X is H, or a biologically compatible cation. As used herein, a biologically compatible cation is a cation that is not toxic as used, and does not have a substantially deleterious effect on biomolecules. Examples of biologically compatible cations include, among others, $K^+$, $Na^+$, $Cs^+$, $Li^+$, $Ca^{2+}$, $Mg^{2+}$, alkylammonium or alkoxyammonium salts, pyridinium salts, or an inner salt with an amine on the coumarin itself.

The compounds of the invention have the general formula:

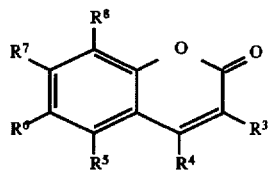

wherein the substituent $R^3$ is H, $SO_3X$, halogen, CN, formyl, or $NO_2$. The substituent $R^4$ is H, CN, alkyl having 1–18 carbons, perfluoroalkyl having 1–18 carbons, or sulfomethyl or biologically compatible salt of sulfomethyl ($CH_2SO_3X$). In one embodiment of the invention, one of $R^3$ and $R^4$ is a reactive group having the formula —L—$R_X$. In another embodiment of the invention, one of $R^3$ and $R^4$ is a conjugated substance having the formula —L—$S_C$. Preferably $R^3$ is H, —L—$R_X$ or —L—$S_C$. Preferably $R^4$ is H, methyl, trifluoromethyl, sulfomethyl, —L—$R_X$ or —L—$S_C$.

The substituent $R^5$ is H.
The substituent $R^6$ is H, methyl, halogen, or $SO_3X$.
As used herein, halogen is Cl, Br, I or F. Preferred halogens are F, Cl or Br.

The substituent $R^7$ is either an amine moiety having the formula $NR^1R^2$, or is formally derived from an amine moiety. The amine substituents $R^1$ and $R^2$ are independently H, alkyl having 1–18 carbons, aryl having 6–18 carbons, alkanoyl having 1–18 carbons, or arylalkanoyl having 7–18 carbons. Alternatively $R^1$ in combination with $R^2$ forms a saturated 5- or 6-membered heterocycle that is a piperidine, a morpholine, a pyrrolidine or a piperazine. Preferably $R^1$ and $R^2$ are independently H, methyl or ethyl.

In another embodiment of the invention, $R^2$ is H and $R^1$ is a radical formed by a removal of the hydroxyl group from the carboxylic acid of an amino acid or from the carboxylic acid of the carboxy-terminal amino acid of a linear peptide consisting of 2–6 amino acids. Preferably, $R^2$ is H and $R^1$ is an amide of an amino acid or peptide that is composed of 1–4 amino acids.

Where $R^1$ is derived from an amino acid, the amino acid is a natural or synthetic amino acid, optionally modified on any free amines by carbobenzyloxy (CBZ), p-toluenesulfonyl (tosyl), succinoyl, glutaroyl, acetyl or other protecting groups so as to yield amides and optionally modified on other side-chain functional groups by esterification or alkylation. Where $R^1$ is derived from a peptide, the sequence of the peptide is selected so as to be a suitable enzyme substrate as is known for other 7-aminocoumarin-based substrates. Preferred substrates are those for aminopeptidases and dipeptidyl peptidases. Particularly preferred are substrates for dipeptidyl peptidases I, II and IV, calpain, elastase, trypsin, chymotrypsin, granzyme A, thrombin, cathepsins, urokinase, kallikrein, human adenovirus proteinase, plasminogen activator, interleukin converting enzyme, amyloid A4-generating enzyme, follipsin and leucine aminopeptidase. In one embodiment, substrates wherein $R^1$ is derived from an amino acid or peptide amide are optionally substituted at $R^3$ or $R^4$ by a reactive group (—L—$R_X$) or a conjugated substance (—L—$S_C$).

In another embodiment of the invention, $R^7$ is formally derived from an amine group by replacing the anomeric oxygen atom of an open-ring mono- or polysaccharide derivative with the amine nitrogen, linked by a single or double covalent bond to the anomeric carbon of the saccharide. When the radical is linked by a double bond, the anomeric oxygen atom has been displaced and $R^7$ is a Schiff's base formed between the aminocoumarin and the reducing sugar. When the radical is linked by a single covalent bond, the anomeric oxygen atom has been displaced and $R^7$ can be considered to be derived via reduction of the above Schiff's base. These compound are typically useful as tagging agents, wherein the sulfonic acid(s) on the coumarin provides the ionic charge required for separation by electrophoretic means and the dye provides the means of detection of the analyte.

Alternatively, $R^2$ is H and $R^1$ is a 2-nitrobenzyloxycarbonyl of the formula

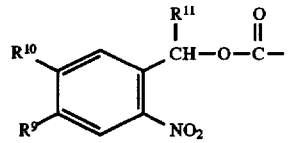

wherein the aromatic substituents $R^9$ and $R^{10}$ are H, alkoxy having 1–6 carbons, or $R^9$ and $R^{10}$ taken in combination are methylenedioxy (—O—$CH_2$—O—). $R^{11}$ is H, $CH_3$, a carboxylic acid or a biologically compatible salt of a carboxylic acid.

The substituent $R^8$ is H, halogen, sulfonic acid or biologically compatible salt of sulfonic acid ($SO_3X$).

For all embodiments of the invention, at least one of $R^3$, $R^6$ and $R^8$ is $SO_3X$. Preferably one of $R^3$ or $R^6$ or both are $SO_3X$. More preferably $R^6$ is $SO_3X$ and both $R^3$ and $R^8$ are not $SO_3X$. In another preferred embodiment, $R^3$ is $SO_3X$ and both $R^6$ and $R^8$ are not $SO_3X$.

In one embodiment, one of $R^3$ and $R^4$ is —L—$R_x$; preferably $R^3$ is —L—$R_X$. In another embodiment of the invention, at least one of $R^3$ and $R^4$ is —L—$S_c$; preferably $R^3$ is —L—$S_C$. In an additional embodiment of the invention, one of $R^3$ or $R^4$ is —L—$R_X$ or —L—$S_C$ and $R^7$ is $NR^1R^2$ where $R^2$ is H and $R^1$ is a radical formed by a removal of the hydroxyl group from the carboxylic acid of an amino acid or from the carboxylic acid of the carboxy-terminal amino acid of a linear peptide consisting of 2–6 amino acids.

Selected embodiments of the present invention are given in Table 1.

TABLE 1
Selected embodiments of the dyes of the present invention
Compound 2 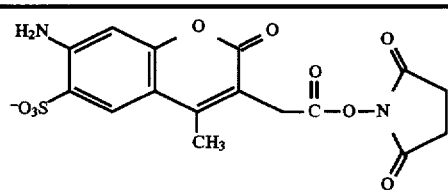
Compound 4 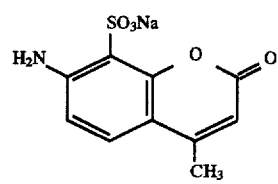
Compound 9 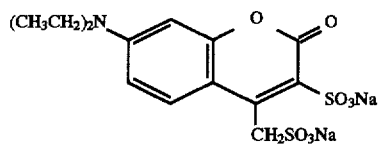
Compound 12a 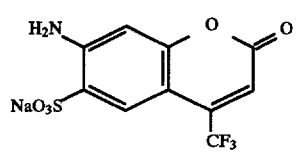
Compound 12b 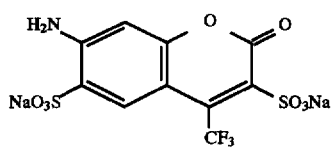
Compound 13a 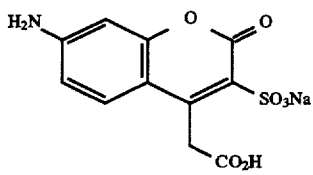
Compound 20 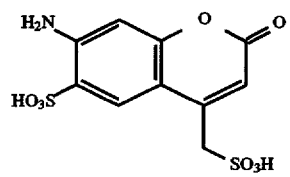
Compound 21 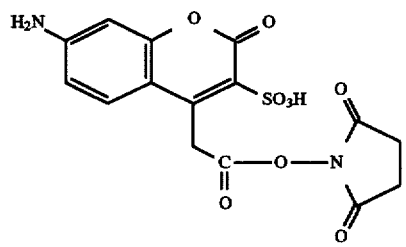
Compound 22 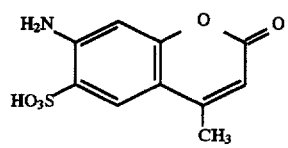

TABLE 1-continued
Selected embodiments of the dyes of the present invention
Compound 23
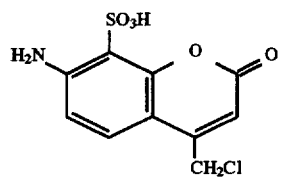
Compound 24
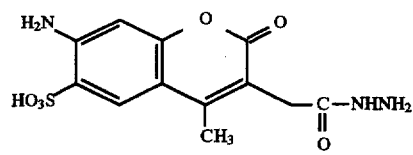
Compound 25
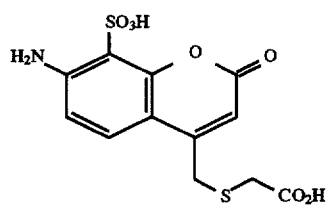
Compound 26
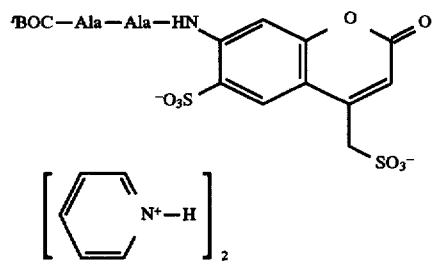
Compound 27
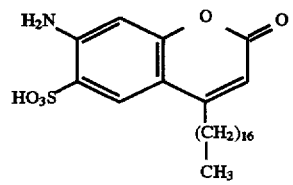
Compound 28
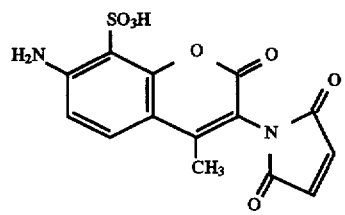
Compound 29
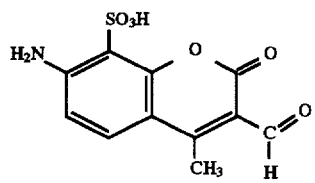

TABLE 1-continued

Selected embodiments of the dyes of the present invention

Compound 30

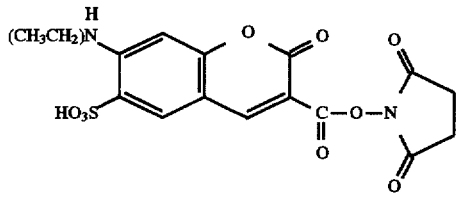

Compound 31

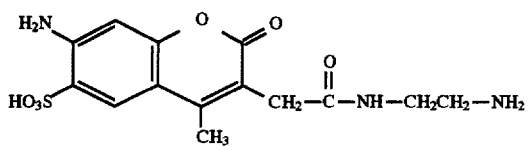

Compound 32

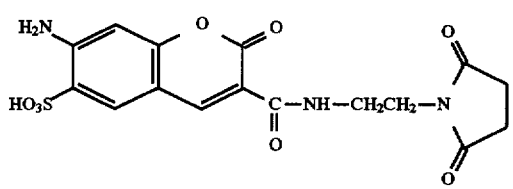

Compound 33

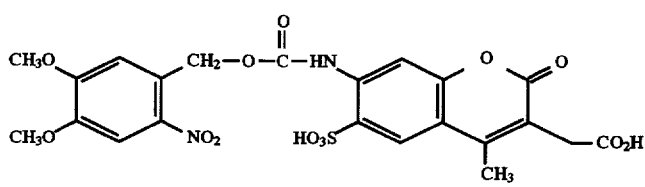

Compound 34

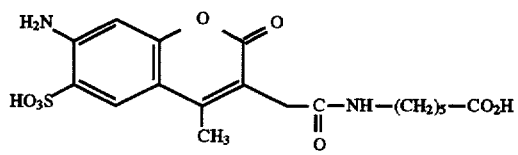

Compound 35

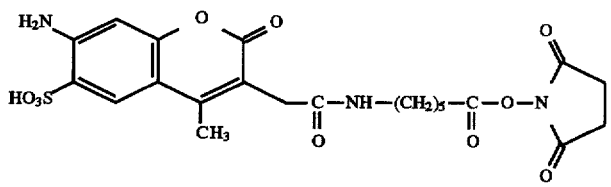

Compound 36

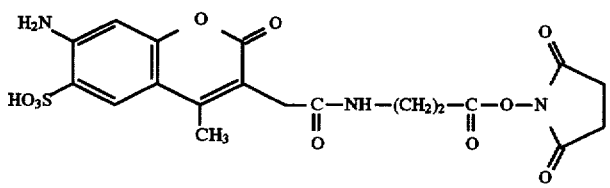

Compound 37

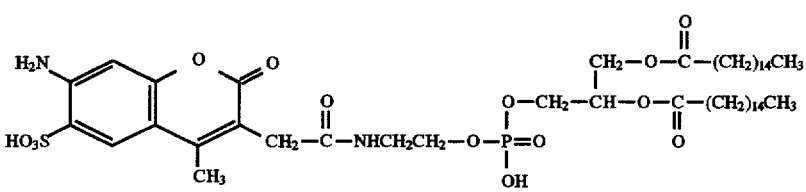

Preparation of sulfonated 7-aminocoumarins

Simple sulfonated derivatives of 7-aminocoumarin are typically prepared by sulfonation of a suitably substituted aminocoumarin dye using pure sulfuric acid or fuming sulfuric acid. As is common for sulfonation reactions, the particular reaction conditions can be varied considerably to affect the pattern and extent of sulfonation, as multiple sites may be sulfonated during the sulfonation reaction. Optimization of a given synthesis requires careful evaluation of the reaction conditions and complete analysis of the reaction products. The following general guidelines serve to broadly outline typical patterns of sulfonation:

Sulfonation of simple 4-alkyl-7-aminocoumarins typically yields complex mixtures of product, including low yields of 4-alkyl-7-aminocoumarin-8-sulfonic acids (as in Example 4). Sulfonation of 7-aminocoumarins that are substituted at the 6-position by halogen or lower alkyl also typically yield sulfonation at the 8-position.

Alternatively, when both the 3- and 4-positions of a 7-aminocoumarin are substituted, sulfonation typically occurs exclusively at the 6-position (as in Example 1).

Sulfonation of a 4-alkyl-7-(dialkylamino)coumarin predominantly yields products wherein sulfonation occurs at the 3-position (as in Example 12).

Additional sulfonation of alkyl substituents at the 4-position has also been observed, in particular facilitating the preparation of 7-amino- (or dialkylamino)-4-sulfomethylcoumarin-3-sulfonic acids (as in Examples 8 and 10).

Where the 4-substituent of the aminocoumarin is perfluoroalkyl, sulfonation of 7-amino-4-perfluoroalkylcoumarins yields predominantly substitution of sulfonic acids at the 6-position, or at both the 6- and 3-positions (as in Example 12).

In another synthetic approach, a sulfonated 7-aminocoumarin can be further alkylated under standard condition, such as by dimethyl sulfate. This is the preferred route to 7-dialkylaminocoumarin-6-sulfonic acid derivatives that are not perfluoroalkylated at $R^4$ and that are not additionally sulfonated at the 3-position.

Sulfonic acids are strong acids and form salts with many organic and inorganic bases. Preferred salts are those that yield nonhygroscopic products and include alkali and alkaline earth metals, ammonium and alkylammonium salts. Typically the product is isolated as a zwitterion with the 7-amine substituent of the coumarin, or as the sodium salt. The exact nature of the counterion is typically not important to the application or the preparation of reactive versions of the dyes or their conjugates but may affect the solubility of the dye in the medium.

Sulfonated aminocoumarins that are further substituted by reactive groups, or conjugated substances, are typically prepared by converting an existing dye substituent into a reactive group or —L—$R_X$. Particularly useful candidates for this conversion include coumarin-3-carboxylic acids, coumarin-3-alkanoic acids and coumarin-4-alkanoic acids, 4-halomethylcoumarins (for example Compounds 13b, 23, 29, and 34 in Table 1). These derivatives are easily converted into activated carboxylic acid esters, amines, thiol-reactive probes, hydrazides and other derivatives using conventional chemistry well understood in the art (see, for instance, Examples 2, 5, and 14).

Dye compounds wherein $R^7$ is a nitrogen atom bound to the anomeric carbon atom of a mono- or polysaccharide are typically prepared in situ via a Schiff base followed by reduction, for example with a borohydride.

Conjugates of Reactive Dyes

The dyes of the invention with a reactive group ($R_X$) fluorescently label a wide variety of organic or inorganic substances that contain or are modified to contain functional groups with suitable reactivity, resulting in chemical attachment of the conjugated substance ($S_C$). The reactive group and functional group are typically an electrophile and a nucleophile that generate a covalent linkage upon contact. Alternatively, the reactive group is a photoactivatable group, and becomes chemically reactive only after illumination with light of an appropriate wavelength. Selected examples of functional groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

* Activated esters, as understood in the art, generally have the formula —COΩ, where Ω is a good leaving group (e.g. oxysuccinimidyl (—OC$_4$H$_4$O$_2$) oxysulfosuccinimidyl (—OC$_4$H$_3$O$_2$—$_{SO3}$H),-1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$–C6 alkyl, C$_1$–C$_6$ perfluoroalkyl, or C$_1$–C$_6$ perfluoroalkyl, or C$_1$–C$_6$ alkoxy; or cyclohexyl, 3-dimethylaminopropyl, or N-morpholinoethyl).
** Acyl azides can also rearrange upon heating to isocyanates The covalent linkage L binds the reactive group $R_X$ or conjugated substance $S_C$ to the fluorophore, either directly or with a combination of stable chemical bonds, optionally including single, double, triple or aromatic carbon-carbon bonds, as well as carbon-nitrogen bonds, nitrogen-nitrogen bonds, carbon-oxygen bonds and carbon-sulfur bonds. Generally, L moieties have 1–24 nonhydrogen atoms selected from the group consisting of C, N, O and S; and are composed of any combination of ether, thioether, amine, ester, carboxamide, sulfonamide, hydrazide bonds and aromatic or heteroaromatic bonds. Preferably, L is a single covalent bond or the longest linear segment of the linkage L preferably contains 4–10 nonhydrogen atoms, of which two or fewer are heteroatoms; and comprises one or more carbonyl, carboxamide, polymethylene or phenylene linkages; or an ether or thioether linkage. Carbonyl means —(C=O)—; carboxamide means —(C=O)—NH— or —NH—(C=O)—; polymethylene means —(CH$_2$)$_n$—, where n=1–12; preferably n=1–5; phenylene means —(C$_6$H$_4$)—, where the points of attachment are typically para to each other on the phenyl ring. An ether or thioether typically has the formula —(CH$_2$)$_a$—Y—(CH$_2$)$_b$—, where a=0–5, b=1–5, and Y is O or S. In yet another embodiment of the invention, L has the formula —(CH$_2$)$_a$—((C=O)—NH—(CH$_2$)$_b$)$_z$—, where a and b are as defined above, and z is 0 or 1.

The selection of covalent linkage to attach the coumarin to the conjugated substance typically depends on the functional group on the substance to be conjugated. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. Although some selectivity can be obtained by careful control of the reaction conditions, selectivity of labeling is best obtained by selection of an appropriate reactive dye.

Typically, $R_X$ is an acrylamide, a carboxylic acid, an activated ester of a carboxylic acid, a hydroxy, an aldehyde, an alkyl halide, a sulfonate, an amine, an anhydride, an aniline, an aryl halide, an azide, an aziridine, a boronate, a carbodiimide, an epoxide, a glycol, a haloacetamide, a halotriazine, a hydrazine, a hydroxylamine, an isothiocyanate, a ketone, a maleimide, a sulfonyl halide, or a thiol group. Preferably, $R_X$ is a carboxylic acid, an activated ester of a carboxylic acid, a hydroxy, an aldehyde, an alkyl halide, an amine, a haloacetamide, a halotriazine, a hydrazine, an isothiocyanate, a maleimide, or a thiol group.

For conjugation to substances having free amine groups, typically dyes are selected wherein L is either a single chemical bond, or L is —(CH$_2$)$_a$—, or L is —(CH$_2$)$_a$—(C=O)(NH(CH$_2$)$_b$)$_z$— or L is —(CH$_2$)$_a$—Y—(CH$_2$)$_b$— (where a, b, z and Y are as defined previously) and $R_X$ is a carboxylic acid or is an activated ester of a carboxylic acid (which is preferably a succinimidyl). Preferably R$^6$ is SO$_3$X, R$^1$, R$^2$ and R$^8$ are each H; and, if R$^3$ is —L—R$_X$, then R$^4$ is methyl and, if R$^4$ is —L—R$_X$, then R$^3$ is H. Examples of amine-reactive dyes include Compounds 2, 21, 30, 35, and 36 in Table 1. Amine-reactive dyes are of particular relevance as they are commonly used to label proteins and polypeptides, which possess free amine groups, or for chemical derivatization of amines to be analyzed by chromatographic or electrophoretic means. Amine-reactive dyes are additionally used to label materials that have been substituted with free amine groups, such as amino-dextrans, or amine-containing nucleotides, oligonucleotides, nucleic acids, amine-derivatized polymers or glasses, amine-containing haptens, or amine-containing drugs.

For conjugation to free thiol groups, dyes of the invention typically have $R_X$ as a haloalkyl (particularly halomethyl), haloacetamide, halomethylbenzamide, a maleimide group, an epoxide or a sulfonate ester, wherein the sulfonic acid is an alkylsulfonic acid, perfluoroalkylsulfonic acid or an arylsulfonic acid. Preferred thiol-reactive dyes of the invention are those wherein R$^3$ is —L—R$_X$ and R$_X$ is maleimido or haloacetamido. Additional preferred thiol-reactive dyes of the invention are those wherein R$^4$ is —L—R$_X$ and R$_X$ is —CH$_2$Cl or —CH$_2$Br or R$_X$ is maleimido, bromoacetamido or iodoacetamido. Examples include Compounds 23, and 28 in Table 1.

Preferred alcohol- and phenol-reactive dyes are those dyes of the invention wherein R$_X$ is a dichloro-s-triazine (e.g. 3,5-dichloro-2,4,6- triazine). In these embodiments, R$^1$ and R$^2$ are typically independently alkyl having 1–6 carbons. Preferred aldehyde- and ketone-reactive groups are hydrazines and carbohydrazides.

Dye-conjugates prepared using photoreactive dyes of the invention (wherein R$_X$ is an azide, diazirinyl, azidoaryl (including azidoperfluoroaryl) derivative) require illumination with a suitable wavelength, typically <400 nm. Preferred photoreactive groups are azidotetrafluorophenyl or azidotetrafluorobenzoyl. Alternatively, dye-conjugates containing photoreactive groups (either of the azide, diazirinyl or azidoaryl photocrosslinking type or of those wherein R$^7$ is a caging moiety) are prepared from derivatives that have an additional reactive moiety —L—R$_X$.

Amine- and hydrazine-containing derivatives of the invention are particularly useful for modifying reducing sugars of mono- and polysaccharides. Where R$^7$ is NR$^1$R$^2$, and R$^1$ and R$^2$ are both H, the aromatic amine at R$^7$ and other aromatic amines that are present in —L—R$_X$, in particular 3-aminocoumarins and 3-aminophenylcoumarins, can be coupled to reducing carbohydrates via a Schiff's base formation (as described above) and used for the characterization of those carbohydrates by electrophoretic techniques such as described for aminonaphthalenesulfonic acids e.g. 8-aminonaphthalene-1,3,6-trisulfonic acid (for example Jackson METH. ENZYMOL. 230, 250 (1994)) and 8-aminopyrene-1,3,6-trisulfonic acid (for example O'Shea et al. ELECTROPHORESIS 17, 681 (1996)). Amines are also preferred reactive groups for conjugation to carboxylic acids and activated esters of carboxylic acids.

Useful dye-conjugates of the present invention include conjugates of antigens, steroids, vitamins, metabolites, toxins, environmental pollutants, tyramine, amino acids, peptides, proteins, nucleic acids, nucleic acid polymers, carbohydrates, lipids, ion-complexing moieties, polymers, or cells or cellular components. Typically, the dye-conjugates are conjugates of peptides or proteins; nucleotides, or nucleic acid polymers; lipids; mono- or polysaccharides; therapeutic drugs and drugs of abuse; and pesticides.

Alternatively, the conjugates of the present invention are conjugates of cells, cellular systems, cellular fragments, or subcellular particles. Typically, in this embodiment of the invention the conjugated materials include virus particles, bacterial particles, virus components, biological cells (such as animal cells, plant cells, bacteria, or yeast), or cellular components.

Most preferably, the conjugated substance is an amino acid, peptide, protein, polysaccharide, ion-complexing moiety, nucleotide, oligonucleotide, nucleic acid, hapten, drug, lipid, phospholipid, lipoprotein, lipopolysaccharide, liposome, lipophilic polymer, polymeric microparticle, animal cell, plant cell, bacterium, yeast or virus.

In one embodiment of the invention, the conjugated substance (S$_C$) is an amino acid or a polymer of amino acids such as a peptide or protein. Amino acids mean natural amino acids or their optical isomers, as well as synthetic variations utilized in the art. Common synthetic variations include amino acids that are protected on their amino, carboxylic acid, hydroxy, thiol, imidazole or other functional group. Other modified amino acids are substituted by phosphate, or through glycosylation or acylation with a $C_1$ to $C_{22}$ carboxylic acid. Peptides generally have molecular weights of less than about 5,000 to 10,000 daltons, and proteins have molecular weights greater than about 5,000 to 10,000 daltons and typically possess secondary, tertiary and/or quaternary structure. Preferred conjugates of peptides contain at least five amino acids, more preferably 5 to 36 amino acids. Preferred peptides to be conjugated to the dyes of the invention include, but are not limited to, neuropeptides, chemotactic peptides, cytokines (such as lymphokines), gastrointestinal peptides, toxins, protease substrates, synthetic peptides, experimental peptides, endothelin and protein kinase substrates. Protein conjugates of the invention include labeled enzymes, antibodies, catalytic antibodies, kinases, lectins, glycoproteins, histones, albumins, lipoproteins, avidin, streptavidin, protein A, protein G, phycobiliproteins, hormones, toxins and growth factors. Typically, the conjugated protein is an antibody, an antibody fragment, avidin, streptavidin, α-bungarotoxin, a lectin, a growth factor, or a phallotoxin.

In another embodiment of the invention, the conjugated substance ($S_C$) is a single nucleic acid base, single nucleoside, single nucleotide or a nucleic acid polymer. A nucleotide comprises an ester of a nucleoside and one or more phosphoric acid or polyphosphoric acid groups, optionally containing an additional linker or spacer for attachment of a fluorophore or other ligand, such as an alkynyl linkage (U.S. Pat. No. 5,047,519 to Hobbs, Jr. et al., (1991), incorporated by reference), an aminoallyl linkage (U.S. Pat. No. 4,711,955 to Ward et al. (1987), incorporated by reference) or other linkage. Nucleotides, as used herein, include natural and synthetic derivatives, including deoxynucleotides, dideoxynucleotides, cyclonucleotides and abasic nucleotide analogs, wherein the base is replaced by a fluorophore or hapten. Preferably, the conjugated nucleotide is a mono-, di- or triphosphate ester of an adenosine, a guanosine, a uridine, a cytidine or a thymidine. More preferably, the conjugated nucleotide is a nucleoside triphosphate or a deoxynucleoside triphosphate or a dideoxynucleoside triphosphate.

Preferred conjugates of nucleic acid polymers are labeled oligonucleotides composed of fewer than 50 nucleotides, more typically composed of fewer than 25 nucleotides. Oligonucleotides are optionally deoxyribonucleic acid polymers (DNA) or ribonucleic acid polymers (RNA), or a hybrid thereof. Nucleic acid polymers are optionally single-stranded or multi-stranded; and may be a natural polymer (biological in origin) or a synthetic polymer (modified or prepared artificially). The nucleic acid polymer optionally incorporates an unusual linker such as morpholine derivatized phosphates (AntiVirals, Inc., Corvallis Oreg.), or peptide nucleic acids such as N-(2-aminoethyl)glycine units (Wittung, et al., NATURE 368, 561 (1994)). In one embodiment of the invention, the dye is attached to the nucleotide, oligonucleotide or nucleic acid polymer via one or more purine or pyrimidine bases through an amide, ester, ether or thioether bond. In another embodiment of the invention, the dye is attached to the phosphate or carbohydrate by a bond that is an ester, thioester, amide, ether or thioether.

In another embodiment of the invention, the conjugated substance ($S_C$) is a carbohydrate, i.e. an organic compound composed of carbon, hydrogen and oxygen and occasionally nitrogen or sulfur, that include sugars, starches and celluloses. The conjugated substance is typically a polysaccharide, such as dextran, FICOL, heparin, glycogen, amylopectin, mannan, inulin, starch, agarose and cellulose, all of which are readily available. Preferred polysaccharide conjugates are dextran or FICOL conjugates, more preferably a dextran conjugate.

In another embodiment of the invention, the conjugated substance ($S_C$), is a lipid. Lipids are long-chain saturated or unsaturated aliphatic hydrocarbons (typically having 6–25 carbons) and their derivatives, such as fatty acids, alcohols, amines, amino alcohols, and aldehydes. The class of lipids includes glycolipids, phospholipids (for example, Compound 37 in Table 1) and sphingolipids. Alternatively, the conjugated substance is a lipid vesicle, such as a liposome, or is a lipoprotein. Alternatively, the dye contains a lipophilic substituent, e.g. where $R^4$ is a linear saturated or unsaturated fatty alkyl group (e.g. Compound 27 in Table 1), typically with 12–18 carbon atoms, wherein one or both of $R^3$ and $R^6$ is $SO_3X$.

One class of conjugates of the present invention includes conjugates of biologically active molecules. Biologically active molecules include, but are not limited to, drugs, toxins, metabolites, pesticides, pollutants and the like. In one embodiment of the invention, the conjugated substance is a drug or toxin. Where the conjugated substance is a drug, preferred drugs of interest are the alkaloids (including morphine alkaloids), steroids, lactams having from 5 to 6 annular members, aminoalkylbenzenes, benzheterocyclics, purines, marijuana-derived drugs, vitamins, prostaglandins, antibiotics and aminoglycosides, as well as their individual derivatives and metabolites. Metabolites related to diseased states include spermine, galactose, phenylpyruvic acid and porphyrin Type 1. Among pesticides of interest are polyhalogenated biphenyls, phosphate esters, thiophosphates, carbamates, polyhalogenated sulfenamides, their metabolites and derivatives.

The conjugated substance is optionally an ion-complexing moiety. Preferred ion-complexing moieties are crown ether, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995), U.S. Pat. No. 5,516,911 to London et al., and U.S. Pat. No. 5,049,673 to Tsien et al. (1991) (all incorporated by reference); derivatives of 2-carboxymethoxyaniline-N,N-diacetic acid (APTRA), as described by Ragu et al. AM. J. PHYSIOL. 256, C540 (1989); and pyridine- and phenanthroline-based metal ion chelators, as described in Copending Application 08/384, 945, filed Feb. 6, 1995 by Kuhn et al. (incorporated by reference). Preferably the conjugated ion-complexing moiety is a diaryldiaza crown ether chelator or a BAPTA chelator.

Conjugates of non-biological polymers are also useful aspects of the invention, including dye-conjugates of synthetic polymers, polymeric particles (including magnetic and non-magnetic microparticles) polymeric membranes, conducting and non-conducting metals and non-metals, and glass and plastic surfaces and particles. Conjugates are optionally prepared by copolymerization of a coumarin dye that contains an appropriate functionality (for example an acrylic acid- or styryl-substituent) while preparing the polymer, or more commonly by chemical modification of a polymer that contains functional groups with suitable chemical reactivity. In another embodiment of the invention, the conjugated substance is a glass or silica, which may be formed into an optical fiber or other structure. Other types of reactions that are useful for preparing dye-conjugates, especially of polymers, include catalyzed polymerizations or copolymerizations of alkenes, reactions of dienes with dienophiles, and transesterifications or transaminations.

The preparation of dye conjugates using reactive dyes is well documented, e.g. by G. T. Hermanson, BIOCONJUGATE TECHNIQUES (Academic Press 1996); and R. Haugland, MOLECULAR PROBES HANDBOOK OF FLUORESCENT PROBES AND RESEARCH CHEMICALS, Sets 1–7 (1992). Brinkley et al., BIOCONJUGATE CHEM., 3, 2 (1992); Haugland et al., METH. MOL. BIOL. 45, 205 (1995)). Conjugates of the invention typically result from simply mixing the appropriate reactive dyes of the present invention and the substance to be conjugated in a suitable solvent in which both are soluble. Unlike the previously described reactive coumarin derivatives of Robinson supra, the reactive dyes of the invention are directly soluble in water at greater than 1 mM. Water solubility is especially advantageous in labeling of living cells and organic solvent-sensitive proteins. The reaction preferably proceeds spontaneously without added reagents at room temperature or below. For those reactive dyes that are photoactivated, conjugation requires illumination of the reaction mixture to activate the reactive dye.

Preparation of conjugates of biological molecules typically comprises first dissolving the biomolecule to be conjugated in aqueous buffer at ~1–10 mg/mL at room temperature or below. Preferred buffers include carbonate buffers pH~8.3 for reaction with succinimidyl esters, phosphate buffers pH~7.2–8 for reaction with thiol-reactive functional groups and carbonate or borate buffers pH~9 for reaction with isothiocyanates and dichlorotriazines. The appropriate reactive dye is then dissolved in water or a water-miscible solvent (usually DMSO or DMF) in an amount sufficient to give a suitable degree of conjugation when added to a solution of the biomolecule to be conjugated. The appropriate amount of dye is predetermined by experimentation in which variable amounts of the dye are added to the biomolecule and unconjugated dye is chromatographically removed (Example 22). For all conjugates, an excess of dye is typically used, relative to the expected degree of dye substitution.

Figure 2:
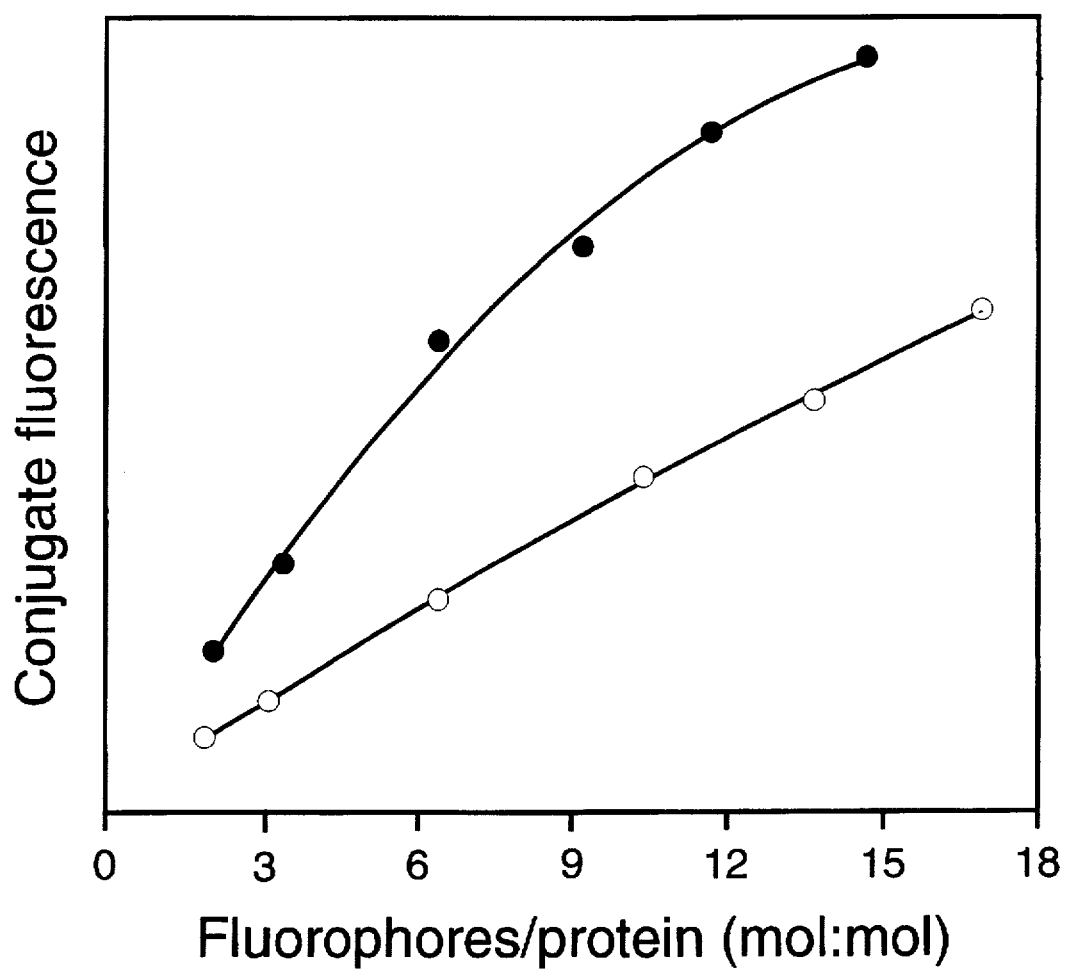
FIG. 2: A comparison of relative fluorescence of streptavidin conjugates of 7-amino-4-methylcoumarin-3-acetic acid, succinimidyl ester (○) and the 7-amino-4-methyl-6-sulfocoumarin-3-acetic acid, succinimidyl ester (Compound 2, ●). Conjugate fluorescence is determined by measuring the fluorescence quantum yield of the conjugated dye relative to that of the free dye and multiplying by the number of fluorophores per protein (as in Example 22). The conjugates of Compound 2 exhibit enhanced fluorescence with respect to the conjugates of the non-sulfonated dye.

Following addition of the reactive dye to the biomolecule, the solution is incubated for a suitable period (typically ~1 hour at room temperature to several hours on ice), the excess dye is removed by gel filtration, dialysis, HPLC, adsorption on an ion exchange or hydrophobic polymer or other suitable means. The dye-biomolecule conjugate is used in solution or lyophilized. The approximate degree of dye substitution is determined from the absorption of the dye-conjugate (Example 22) or by using the dry weight of the conjugate. The fluorescence in measured as a function of degree of dye substitution (for instance as in Example 23 and FIGS. 2 and 3).

Conjugates of amino acids and peptides through $R^7$ so as to provide enzyme substrates are prepared by organic synthesis using means extensively described for preparation of similar substrates from 7-amino-4-methylcoumarin. Typically, single amino acids suitably protected on their side-chain substituents are conjugated to the 7-aminocoumarinsulfonic acid to form the first amino acid amide then, if appropriate, deprotected and coupled in multiple steps with 1–5 additional amino acids using methods well known in the art of peptide synthesis.

In one aspect of the invention, the conjugate of the invention is associated with an additional substance, that binds either to the fluorophore or the conjugated substance through noncovalent interaction. In a specific embodiment, the additional substance is an antibody to the dye, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

In another embodiment of the invention, one of the reactive dyes of the invention is provided in one or more suitable containers with instructions for conjugating the dye to any substance possessing an appropriate functional group, and optionally for recovering or purifying the materials labeled thereby. This combination of reactive dye and instructions therefore comprise a kit for labeling an appropriate substance. Selected appropriate substances include, but are not limited to, polymers of biological molecules (e.g. proteins, oligonucleotides or carbohydrates), polymeric resins and plastics (e.g. polystyrene), metals, glasses, and other organic or inorganic substances. The dyes of the present invention are well-suited for the preparation of such a kit.

Applications and Methods of Use

The dye compounds of the invention are generally utilized by combining an aminocoumarin sulfonic acid derivative described above with the sample of interest under conditions selected to yield a detectable optical response. The term "dye compound" is used herein to refer to all aspects of the claimed sulfonated aminocoumarins, including reactive sulfonated aminocoumarins, conjugates of sulfonated aminocoumarins, lipophilic versions of sulfonated aminocoumarins, substituted sulfonated aminocoumarins for use as enzyme substrates, and additional derivatives. The dye compound typically forms a covalent or non-covalent association or complex with an element of the sample, or is simply present within the bounds of the sample or portion of the sample. Optionally, the sample is washed to remove residual, excess or unbound dye compound. The sample is then illuminated at a wavelength selected to elicit the optical response. Typically, staining the sample is used to determine a specified characteristic of the sample by further comparing the optical response with a standard or expected response.

For biological applications, the dye compounds of the invention are typically used in an aqueous or aqueous-miscible solution prepared according to methods generally known in the art. The exact concentration of dye compound is dependent upon the experimental conditions and the desired results, but typically ranges from about one nanomolar to one millimolar or more. The optimal concentration is determined by systematic variation until satisfactory staining with minimal background fluorescence is accomplished.

The dye compound is combined with the sample in any way that facilitates contact between the dye compound and the sample components of interest. Typically, the dye compound or a solution containing the dye compound is simply added to the sample. Unlike other coumarin derivatives, sulfonated aminocoumarin derivatives tend to be impermeant to membranes of biological cells, and once inside viable cells are typically well retained. Treatments that permeabilize the plasma membrane, such as electroporation, shock treatments or high extracellular ATP can be used to introduce dye compounds into cells. Alternatively, the dye compounds are physically inserted into cells, e.g. by pressure microinjection, scrape loading, patch clamp methods, or phagocytosis. Sulfonated aminocoumarins that incorporate an amine or a hydrazine residue (for example Compound 24 in Table 1) can be microinjected into cells, where they can be fixed in place by aldehyde fixatives such as formaldehyde or glutaraldehyde. Nonsulfonated coumarins are not suitable for such applications because they are not well retained in living cells.

Solubilization of the fluorophore in water by the sulfonic acid and their impermeance to membranes gives the dye compounds of the invention particular utility as polar tracers, according to methods generally known in the art for other dye compounds, see e.g. U.S. Pat. No. 4,473,693 to Stewart (1984) (using lucifer yellow) and U.S. Pat. No. 5,514,710 to Haugland et al. (1996) (using caged hydroxypyrenesulfonic acids) (both patents incorporated by reference). Photolabile or "caged" conjugates permit temporal or spatial control of the fluorogenic compounds. Sulfonated aminocoumarins substituted at $R^1$ by a caging moiety, in particular a 2-nitrobenzyloxycarbonyl substituent (Compound 33 in Table 1 or as in Example 15) exhibit strongly quenched fluorescence properties. The fluorescence of the aminocoumarin is restored by photolysis of the caged probe with ultraviolet light. In this reaction the initially formed N-carboxy derivative spontaneously decomposes to a fluorescent derivative wherein $R'$ is H. Relative to conventional caged coumarins, the dye compounds of the invention have enhanced photostability and are better able to withstand the intense illumination typically required to photolyze the caging group.

Dye compounds that possess a lipophilic substituent at $R^4$ or that are conjugated to lipophilic molecules such as phospholipids will non-covalently incorporate into lipid assemblies, e.g. for use as probes for membrane structure; or for incorporation in liposomes, lipoproteins, films, plastics, lipophilic microspheres or similar materials; or for tracing. Sulfonated aminocoumarin dyes wherein $R^4$ is a fatty alkyl group are useful as fluorescent probes of membrane structure, wherein the sulfonic acid moiety permits trapping of the probe at or near the membrane's surface.

Chemically reactive dye compounds will covalently attach to a corresponding functional group on a wide variety of materials, forming dye conjugates as described above. Using dye compounds to label reactive sites on the surface of cells, in cell membranes or in intracellular compartments such as organelles, or in the cell's cytoplasm, permits the determination of their presence or quantity, or their spatial and temporal distribution in the sample. Unlike other reactive coumarin derivatives, chemically reactive sulfonated aminocoumarin derivatives tend to be impermeant to membranes of biological cells, giving them utility as fluorescent probes for assessing the topography of protein distribution in living cells. Photoreactive sulfonated aminocoumarins can be used similarly to photolabel components of the outer membrane of biological cells or as photo-fixable polar tracers for cells. Outside of the cellular milieu, the negative charge of the dye compounds at neutral pH also facilitates the electrophoretic separation of dye-conjugates of carbohydrates, drugs and other low molecular weight compounds for analysis by capillary zone electrophoresis (CZE), HPLC or other separation techniques. Precipitation of the conjugate is minimized, even after labeling with multiple fluorophores, since the sulfonated aminocoumarin derivatives are fully ionized at neutral pH.

Alternatively, the dye compound is a conjugate of a specific binding pair member, and is used as a fluorescent probe for the complementary member of that specific binding pair, each specific binding pair member having an area on the surface or in a cavity which specifically binds to and is complementary with a particular spatial and polar organization of the other. Representative specific binding pairs are shown in Table 3. The dye compounds are useful as probes for a complementary binding pair member present in an animal cell, plant cell, bacteria, yeast or virus. Alternatively, the complementary member is immobilized on a solid or semi-solid surface, such as a polymer, polymeric membrane or polymeric particle (such as a polymeric bead). The dye compound may also include a moiety at $R^7$ that is later removed by the action of an enzyme or light, such as a peptide or a caging group.

TABLE 3

| Representative Specific Binding Pairs | |
|---|---|
| antigen | antibody |
| biotin | avidin (or streptavidin or anti-biotin) |
| IgG* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | aDNA (aRNA)† |
| hormone | hormone receptor |
| ion | chelator |

*IgG is an immunoglobulin
†aDNA and aRNA are the antisense (complementary) strands used for hybridization The dye conjugates are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. Nos. 5,332,666 to Prober, et al. (1994); 5,171,534 to Smith, et al. (1992); 4,997,928 to Hobbs (1991); and WO Appl. 94/05688 to Menchen, et al.; all incorporated by reference). In one embodiment, dye conjugates of the invention are simultaneously labeled with one or more additional dyes, that may be the same or different. In one embodiment, a conjugate is labeled with two or more different dyes that are selected so as to undergo energy-transfer, and analysis of the spectral properties of the conjugate indicates a mechanism or component of the sample, such as in a double labeled peptide, a double-labeled oligonucleotide or a double-labeled protein. Alternatively, the dye-conjugate is simultaneously labeled with a hapten such as biotin or digoxigenin or other detectable label. Where the labeled specific binding pair member is a chelator of calcium, sodium, magnesium, potassium, or other biologically important metal ion, the dye-conjugate functions as an indicator of the ion, which indicators are optionally further conjugated to a biological or plastic polymer according to methods known in the art. One or more sulfonated aminocoumarin dyes conjugated to a biologically compatible polymer, including amino acid polymers (typically proteins, including fluorescent proteins), carbohydrate polymers (typically dextrans), and polymeric microspheres (typically polystyrene) are readily prepared for use as tracers according to methods known in the art, with the solubility advantages described previously. Where the sulfonated aminocoumarin is conjugated to a tyramine as $S_c$, the resulting dye-conjugate is useful as a substrate for peroxidase enzymes (as described in U.S. Pat. No. 5,196,306 to Bobrow et al. (1993)).

The use of sulfonated aminocoumarins also results in improved fluorogenic enzyme substrates with the appropriate enzyme-cleavable substituent at $R^7$. The increased solubility of the substrate dye compounds is particularly advantageous if the clearable substituent has a low solubility. The enzyme probes of the invention yield products having enhanced fluorescence yield following the enzymatic reaction, relative to their non-sulfonated analogs. Amides of the sulfonated 7-aminocoumarins of the invention also have strongly quenched fluorescence and absorption that is shifted toward the ultraviolet, similar to non-sulfonated derivatives, but their greater water solubility permits preparation of more concentrated aqueous solutions of the substrate, which is beneficial for obtaining pseudo first-order hydrolysis kinetics. Concentrations of dye-conjugates that have utility as enzyme substrates are preferably above the Michaelis-Menton constant ($K_m$) of the enzyme that is being measured, which concentrations are typically in the micromolar to millimolar range.

The sample is optionally combined with one or more other solutions in the course of staining, including wash solutions, permeabilization and/or fixation solutions, and solutions containing additional detection reagents. Where the additional detection reagent has, or yields a product with, spectral properties that differ from those of the subject dye compounds, multi-color applications are possible. Dye compounds of the invention typically have bright blue to blue-green fluorescence (see Table 4) that contrasts well with reagents that give green, yellow, orange or red fluorescence.

TABLE 4

Spectral properties of selected embodiments of the invention

| Compound | Absorbance max. (nm) | $\epsilon \times 10^{-3}$ ($cm^{-1}M^{-1}$) | Emission max. (nm) |
|---|---|---|---|
| 1 | 350 | 19 | 434 |
| 4 | 353 | 19 | 421 |
| 8 | 413 | 26 | 511 |
| 9 | 422 | 27 | 515 |
| 12a | 371 | 18 | 483 |
| 12b | 360 | 18 | 473 |

At any time after or during staining, the sample is illuminated with a wavelength of light selected to give a detectable optical response, and observed with a means for detecting the optical response. Upon UV illumination the dye compounds display intense absorption as well as visible fluorescence emission. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

The examples below are given so as to illustrate the practice of this invention. They are not intended to limit or define the entire scope of this invention.

EXAMPLES

Example 1

Preparation of 7-amino-3-carboxymethyl-4-methylcoumarin-6-sulfonic acid, sodium salt (1)

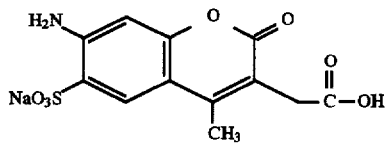

Powdered ethyl 7-ethoxycarbonylamino-4-methylcoumarin-3-acetate (U.S. Pat. No. 3,008,969 to Pretka (1961)) (8 g) is added in small portions with stirring to 30% fuming sulfuric acid (10 mL) that is cooled in an ice/water bath. After the addition is complete, the mixture is stirred for 1 hr at 0° C., warmed to room temperature for 2 hours, and then stirred for 3 days at 70° C. The solution is cooled to room temperature and poured into crushed ice (80 g). After standing overnight at room temperature, the resulting precipitate is collected by suction filtration. The precipitate is resuspended in water (20 mL) and the pH of the suspension is adjusted to about 5 by addition of 2M NaOH. The resulting mixture is poured into 1 L of methanol and the suspension is filtered. The filtrate is evaporated to dryness to give crude product, which is further purified on a SEPHADEX LH-20 resin column eluting with water to give 1.75 g (23%) of pure Compound 1. $^1$H NMR ($d_6$-DMSO) δ7.84 (s, 1H); 6.49 (s, 1H); 5.18 (br s, 2H); 3.4 (s (overlapping with $H_2O$ peak), 2H); 2.34 (s, 3H).

Example 2

Preparation of 7-amino-4-methyl-3-(((succinimidyl)oxy)carbonyl)methyl)-coumarin-6-sulfonic acid, N,N-diisopropylethylammonium salt (2)

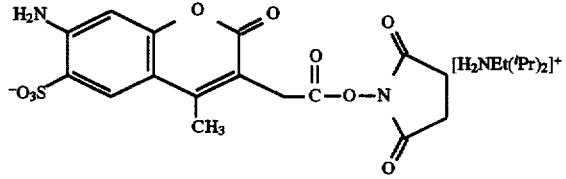

To a solution of 1 (1.02 g, 3.26 mmol) in DMF (20 mL) is added 2-succinimido-1,1,3,3-tetramethyluronium tetrafluoroborate (1 g, 3.58 mmol) and N,N-diisopropylethylamine (0.89 g, 6.89 mmol). The solution is stirred at room temperature for 30 min and then concentrated to dryness by vacuum distillation. The crude solid product is purified by flash column chromatography on silica gel eluting with 5% $H_2O/CH_3CN$ to give 1.15 g (65%) of 2 as a pale orange solid. $^1$H NMR ($d_6$-DMSO) δ7.84 (s, 1H); 6.52 (s, 1H); 3.97 (s, 2H); 3.62–3.58 (m, 2H); 3.12–3.06 (m, 2H); 2.78 (s, 4H); 2.32 (s, 3H); 1.25–1.23 (m, 15H).

Example 3

Preparation of 7-amino-4-methyl-3-(((succinimidyl)oxy)carbonyl)methyl)coumarin-6-sulfonic acid (3)

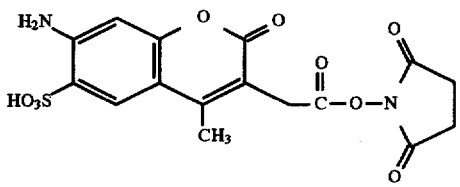

To 1 (1.2 g, 3.83 mmol) in 30 mL dry pyridine is added 2-succinimido-1,1,3,3-tetramethyluronium tetrafluoroborate in small portions over 5 min. After the solution is stirred for 5 hrs, the solvent is removed by vacuum distillation at room temperature. The gummy solid is triturated with ether 6 times (6×50 mL) and then dried overnight under high vacuum at room temperature. The crude material is subjected to silica gel column chromatography eluting with $H_2O/CH_3CN$ (0–6% $H_2O/CH_3CN$). Fractions containing the product are pooled and concentrated to about 15 mL by rotary evaporation at 40° C. After the mixture is cooled to room temperature, the resulting pale yellow precipitate is collected by suction filtration, followed by drying under high vacuum at room temperature for 24 hrs to give 0.5 g of 3. $^1H$ NMR ($d_6$-DMSO with $D_2O$ exchange) δ7.83 (s, 1H); 6.52 (s, 1H); 3.97 (s, 2H); 2.78 (s, 4H); 2.32 (s, 3H).

Example 4

Preparation of 7-amino-4-methylcoumarin-8-sulfonic acid, sodium salt (4)

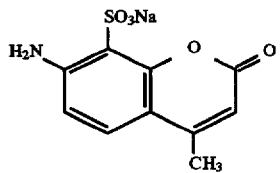

To 30% fuming sulfuric acid (3 mL) stirred at 0° C. is added 7-amino-4-methylcoumarin (0.8 g, 4.57 mmol) in one portion. The mixture is stirred at 0° C. for 30 min, then warmed to 60°–70° C. and stirred overnight. After the solution is cooled to room temperature, dioxane (6 mL) is added, followed by the addition of 40 mL of diethyl ether. The resulting precipitate is collected by suction filtration and then suspended in $H_2O$ (50 mL). The pH of the suspension is adjusted to about 5 by adding $NaHCO_3$. The solvent is removed by rotary evaporation to give a crude solid, which is purified using column chromatography on silica gel, eluting with $H_2O/CH_3CN$ to give 0.25 g (20%) of Compound 4. $^1H$ NMR ($d_6$-DMSO with $D_2O$ exchange) δ7.35 (d, 1H); 6.62 (d, 1H); 5.91 (s, 1H); 2.33 (s, 3H).

Example 5

Synthesis of 7-amino-3-((((2-maleimidyl)ethylamino)carbonyl)methyl)-4-methylcoumarin-6-sulfonic acid (5)

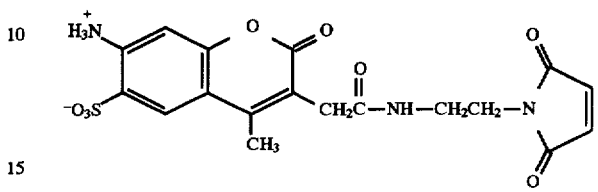

A mixture of Compound 3 (100 mg, 0.24 mmol), N,N-diisopropylethylamine (123 mg, 0.96 mmol) and N-(2-aminoethyl)maleimide trifluoroacetic acid salt (70.8 mg, 0.25 mmol) in DMF (1 mL) is stirred at room temperature overnight. Diethyl ether is added to the reaction mixture, resulting in formation of a precipitate. The resulting solid is filtered and washed with diethyl ether. The crude product is purified by column chromatography on silica gel eluting with 5% $H_2O$ in acetonitrile to give Compound 5 (70 mg, 67%). $^1H$-NMR ($d_6$-DMSO): δ=7.78 (1H, s); 7.0 (2H, s); 6.47 (1H, s); 6.35 (2H, s); 3.46 (2H, m); 3.20 (2H, m), 2.20 (3H, s).

Example 6

Synthesis of 7-amino-3-(((5-carboxylpentylamino)carbonyl)methyl)-4-methylcoumarin-6-sulfonic acid (6)

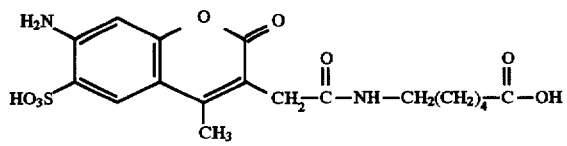

A solution of Compound 3 (70 mg, 0.17 mmol) in DMF (0.3 mL) is added to a solution of 6-aminocaproic acid (41 mg, 0.31 mmol) and $K_2CO_3$ (40 mg, 0.28 mmol) in water (0.3 mL). After the reaction mixture is stirred at room temperature for 1 hr, the solvent is removed under reduced pressure. Methanol is added to the residue, which is then filtered to remove insoluble salts. The resulting filtrate is concentrated to 1 mL and then purified on silica gel column eluting with $CHCl_3$ followed by 5% $H_2O$ in acetonitrile to give Compound 6 (60 mg, 87%). $^1H$-NMR ($d_6$-DMSO): δ=7.80 (1H, s); 6.45 (1H, s); 6.31 (2H, s); 3.40 (2H, s); 3.0 (2H, m), 2.21 (3H, s); 2.10 (2H, m); 1.48 (2H, m); 1.39 (2H, m); 1.24 (2H, m).

Example 7

Synthesis of 7-amino-4-methyl-3-((((((succinimidyl)oxy)carbonyl)pentyl)amino)carbonyl)methyl)coumarin-6-sulfonic acid (7)

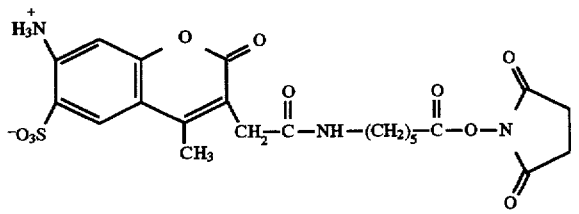

To a solution of Compound 6 (66 mg, 0.14 mmol) in dry DMF (1 mL) is added 1,3-diisopropylcarbodiimide (32 mg, 0.27 mmol) and N-hydroxysuccinimide (30 mg, 0.27 mmol). The reaction mixture is stirred at room temperature overnight, and then precipitated by the addition of diethyl ether. The resulting solid is filtered and washed with diethyl ether. The crude product is purified by column chromatography on silica gel eluting with 5% $H_2O$ in acetonitrile to give 7 (30 mg). $^1$H-NMR ($d_6$-DMSO): δ=7.80 (1H, s); 6.5 (1H, s); 6.35 (2H, s); 3.40 (2H, s); 3.02 (2H, m), 2.80 (4H, s); 2.65 (2H, m); 2.25 (3H, s); 1.62 (2H, m); 1.42–1.35 (4H, m).

Example 8

Synthesis of 7-dimethylamino-4-sulfomethylcoumarin-3-sulfonic acid (8)

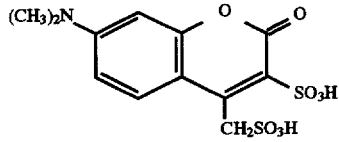

7-Dimethylaminocoumarin-4-acetic acid (2.3 g, 8.8 mmol; Molecular Probes, Inc., Eugene Oreg.) is added in small portions to 30% fuming sulfuric acid (5 mL) at 0° C., and stirred at 70° C. overnight. The reaction mixture is cooled to below −20° C. Water (5 mL) is slowly added and the reaction mixture is then poured into $CH_3CN$. The resulting oily precipitate is dissolved in methanol, and slowly poured into $CH_3CN$. The resulting crude solid is filtered and washed with $CH_3CN$. The product is crystallized from methanol to give pure Compound 8 (2.0, 78%). $^1$H-NMR ($d_6$-DMSO): δ=7.90 (1H, dd); 6.68 (1H, dd); 6.41 (1H, d); 5.02 (2H, s); 3.0 (6H, s).

Example 9

7-Diethylamino-4-sulfomethylcoumarin-3-sulfonic acid, disodium salt (9)

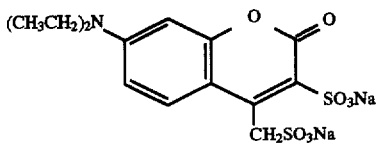

7-Diethylamino-4-methylcoumarin (4.66 g, 10 mmol) is added in small portions to 30% fuming sulfuric acid (5 mL) at 0° C., and the resulting solution is stirred at 70°–90° C. overnight. After cooling to room temperature, the reaction mixture is poured into crushed ice (10 g), and allowed to stand overnight at room temperature. The resulting precipitate is collected by suction filtration. The crude product is dissolved in 2M NaOH and then purified by chromatography on a SEPHADEX LH-20 resin column to give pure Compound 9 (2 g). $^1$H-NMR ($d_6$-DMSO): δ=7.90 (1H, dd); 6.65 (1H, dd); 6.36 (1H, d); 5.18 (2H, s); 3.41 (4H, q); 1.10 (6H, t).

Example 10

Synthesis of 7-amino-4-sulfomethylcoumarin-3-sulfonic acid (10)

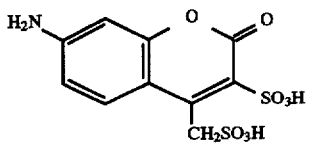

7-Aminocoumarin-4-acetic acid (1.5 g, 6.8 mmol; Besson HETEROCYCLES, 34, 273 (1992)) is dissolved in 30% fuming sulfuric acid (3 mL) at 0° C., and then stirred at 70° C. overnight. After cooling to room temperature, the reaction mixture is poured into a minimum amount of crushed ice (5 g). The resulting solution is purified by chromatography on a SEPHADEX LH-20 resin column eluting with water. The pure fractions are pooled and lyophilized to give pure Compound 10 (0.8 g, 39%). $^1$H-NMR ($d_6$-DMSO): δ=7.75 (1H, dd); 6.56 (1H, dd); 6.32 (1H, d); 5.01 (2H, s).

Example 11

Synthesis of a peptide conjugate of 7-amino-4-sulfomethylcoumarin-3-sulfonic acid, pyridinium salt (11)

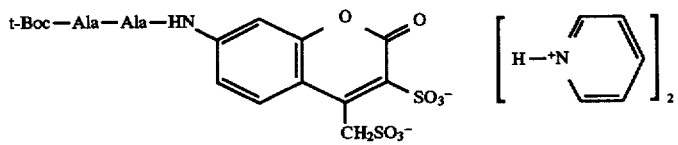

To a solution of t-Boc-Ala-Ala (1.16 g, 5 mmol) in DMF/pyridine (2 mL/2 mL) stirred at 4° C. is added EDAC (1.0 g, 5 mmol), and the reaction mixture is stirred at 4° C. for 30 minutes. To this reaction mixture is added Compound 10 (0.3 g, 1 mmol) in DMF (1 mL) and the resulting mixture is stirred at 4° C. for 2 hours, then at room temperature for 2 days. The solvent is then removed under reduced pressure, and to the resulting residue is added diethyl ether to precipitate the desired product. The crude compound is purified by chromatography on a SEPHADEX LH-20 resin column eluting with water to give Compound 11.

Example 12

Synthesis of 7-amino-4-trifluoromethylcoumarin-6-sulfonic acid, sodium salt (12a) and 7-amino-4-trifluoromethylcoumarin-3,6-disulfonic acid, disodium salt (12b):

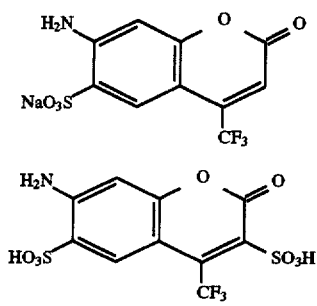

7-Amino-4-trifluoromethylcoumarin (1.5 g, 6.8 mmol) is dissolved in 30% fuming sulfuric acid (3 mL) at 0° C., and then stirred at 70° C. overnight. After cooling to room temperature, the reaction mixture is poured into a minimum amount of crushed ice (5 g). A precipitate forms after standing at room temperature overnight. The solid product is collected by filtration, then dissolved in 1 mL of 2M NaOH and purified by chromatography on a SEPHADEX LH-20 resin column eluting with water to give Compound 12a (0.6 g) and Compound 12b (0.1 g). 12a $^1$H-NMR (d$_6$-DMSO): δ=8.10 (1H, s); 6.72 (1H, s); 6.50 (1H, s). $^{19}$F-NMR (d$_6$-DMSO): δ=−62.3 ppm. 12b $^1$H-NMR (d$_6$-DMSO): δ=7.88 (1H, s); 6.52 (1H, s). $^{19}$F-NMR (d$_6$-DMSO): δ=−58.7 ppm

Example 13

Preparation of 7-amino-4-carboxymethylcoumarin-3-sulfonate sodium salt (13a) and (7-aminocoumarin-4-yl)carboxymethanesulfonate sodium salt (13b)

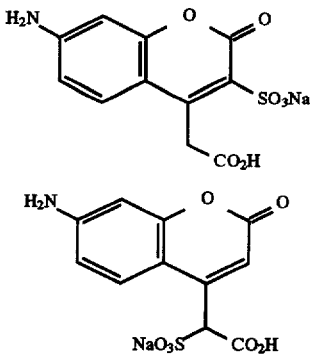

To 30% fuming sulfuric acid (1 mL) at 0° C. is added 7-aminocoumarin-4-acetic acid (100 mg, 0.46 mmol) in one portion. The solution is warmed to room temperature and stirred overnight. The mixture is poured into crushed ice (20 g) and the pH is adjusted to 5–6 by adding powdered NaHCO$_3$. MeOH (150 mL) is added to the above solution, followed by suction filtration. The filtrate is rotary evaporated to dryness to give a crude mixture of Compound 13a (R$_f$=0.47; 15% H$_2$O/CH$_3$CN) and Compound 13b (R$_f$=0.28; 15% H$_2$O/CH$_3$CN), which is purified by chromatography on a SEPHADEX LH-20 resin column eluting with H$_2$O to give a pure mixture. Compounds 13a and 13b are separated by chromatography on a silica gel column eluting with H$_2$O/CH$_3$CN. $^1$H NMR (d$_6$-DMSO with D$_2$O exchange) for 13a δ7.65 (d, J=9 Hz, 1H); 6.67 (d, J=9 Hz, 1H); 6.66 (s, 1H); 3.92 (s, 2H). $^1$H NMR (d$_6$-DMSO with D$_2$O exchange) for 13b δ7.54 (d, J=9 Hz); 6.66 (d, J=9 Hz); 6.55 (s, 1H); 6.06 (s, 1H); 5.06 (s, 1H).

Example 14

Preparation of 7-amino-4-(((succinimidyl)oxy)carbonyl)methylcoumarin-3-sulfonic acid, inner salt (14)

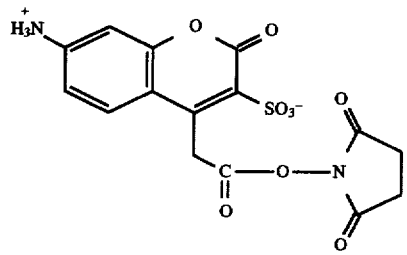

Compound 14 is prepared from Compound 13a according to the procedure described in Example 3.

Example 15

Preparation of 7-(4,5-dimethoxy-2-nitrobenzyloxycarbonylamino)-3-sulfo-4-sulfomethylcoumarin pyridinium salt (15)

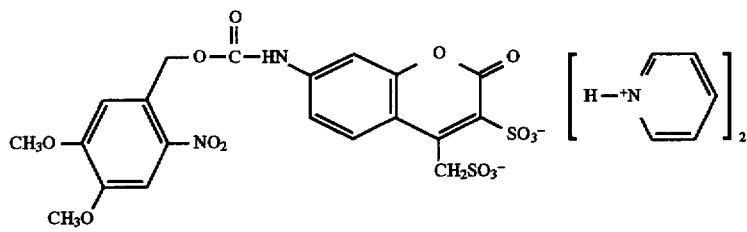

To a solution of Compound 10 (31 mg, 0.1 mmol) in a 1:1 mixture of anhydrous DMF and pyridine (3 mL) stirred at 0° C. is added 4,5-dimethoxy-2-nitrobenzylchloroformate (62 mg, 0.22 mmol) in 1 mL anhydrous THF. The reaction mixture is stirred at 0° C. for 2 hours and then at room temperature overnight. The solvent is removed under high vacuum to give a crude product, which is purified on a silica gel column eluting with 10% $H_2O/CH_3CN$.

Example 16

Preparation of 7-amino-4-methyl-3-nitrocoumarin-8-sulfonic acid (16)

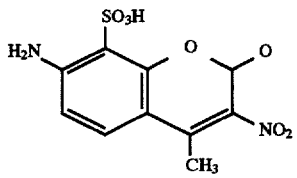

To a solution of Compound 4 (0.5 g) in 15 mL acetic acid at 0° C. is added 1.2 equivalents of 70% $HNO_3$. The reaction mixture is warmed to room temperature, then stirred overnight. The solvent is removed under vacuum, and the residue is purified by chromatography on silica gel eluting with 10% $H_2O/CH_3CN$, to give Compound 16.

Example 17

A comparison of photostability of sulfonated vs. non-sulfonated coumarins

Methanol solutions of Compound 1 and 7-amino-4-methylcoumarin-3-acetic acid (AMCA), respectively, have proven stable at room temperature when carefully shielded from exposure to light. However, when methanol solutions of each dye are exposed to ambient light for 72 hours (room temperature), the AMCA solution becomes yellow in color, while the solution of Compound 1 remains colorless. Thin layer chromatographic analysis ($CHCl_3$:MeOH:HOAc= 8:1.8:0.2) of each solution indicates that the AMCA solution contains three new weakly fluorescent products, each having a higher $R_f$ value than AMCA, while the solution of Compound 1 contains essentially only Compound 1.

Example 18

Preparation of a nucleotide conjugate of 7-amino-6-sulfocoumarin-3-acetic acid, succinimidyl ester (17)

To a solution of 2 mg of 5-(3-aminoallyl)-2'-deoxyuridine-5'-triphosphate, ammonium salt (Sigma Chemical) in 300 μL of water is added a solution of 4 mg of Compound 2 (Example 2) in 150 μL of DMF, followed by the addition of 5 μL of triethylamine. After the mixture is stirred at room temperature for 3 hours, it is purified by chromatography over lipophilic SEPHADEX resin using water for elution. The desired fractions are combined and lyophilized to give the fluorescent nucleotide conjugate as an off-white solid.

Example 19

Preparation of an oligonucleotide conjugate of Compound 2

A sample of 500 μg of a 5'-amine-modified, 24-base M13 primer sequence is dissolved in 220 μL of 0.1M borated sodium bicarbonate pH 8.5 aqueous buffer in a microcentrifuge tube. To this oligonucleotide solution is added a solution of 1 mg of Compound 2 (Example 2) in 35 μL of DMF. The reaction mixture is shaken by hand for a few minutes and allowed to stand at room temperature for 16 hours. To the mixture is added 15 μL of 5M NaCl and 3 volumes of cold 100% ethanol. The resulting mixture is incubated at −20° C. for 30–60 minutes, and then microcentrifuged for 15–30 minutes at 4° C. (5,000–10,000 g). After microcentrifugation, the ethanol supernate is decanted, and the pellet is resuspended in 100 μL $H_2O$. The labeled oligonucleotide is then purified by HPLC on a 220 mm×10 mm 300 ÅC8 reverse phase column (Rainin Instrument Co., Woburn, Mass.) using the following gradient: Solvent A—0.1M TEAA (pH~7), Solvent B—acetonitrile. Ramp Solvent B from 15% to 60% over 30 minutes. Detection is accomplished using a Waters 490 dual wavelength UV-Vis detector monitoring 254 nm and 340 nm. The desired peak is collected and evaporated to yield the fluorescent oligonucleotide.

Example 20

Preparation of a phalloidin conjugate of Compound 2

To a solution of 3 mg of aminophalloidin p-toluenesulfonate and 4 mg of Compound 2 in 300 μL of DMF is added 5 μL of triethylamine and the mixture is stirred at room temperature for 1 hour. To the reaction mixture is added 7 mL of ether and the resulting precipitate is collected by centrifugation. The crude product is purified by chromatography over lipophilic SEPHADEX resin using water for elution. The desired fractions are combined and lyophilized to give the fluorescent phalloidin conjugate as a off-white solid.

Example 21

Preparation of a biocytin conjugate of Compound 2

Biocytin (Molecular Probes, Inc., Eugene, Oreg.) (74.4 mg, 0.2 mmol) and 8 mg NaOH are dissolved in 1 mL water. To the resulting clear solution is added 125 mg (approx. 0.2 mmol) Compound 2 dissolved in 1 mL dimethylformamide.

After stirring 2 hours at room temperature, the solution is diluted with 50 mL water and acidified with 1 mL of 1M HCl. The resulting product is collected by centrifugation, washed well with water and dried. The biocytin-dye conjugate is purified by chromatography on silica gel using mixtures of chloroform and methanol for elution. The pure conjugate is characterized by the formation of a fluorescent complex when the conjugate is treated with excess avidin. The resulting complex comigrates with unlabeled avidin on a SEPHADEX G 100 resin filtration column.

Example 22

Preparation of protein conjugates

Protein conjugates of Compound 2 and 7-amino-4-methylcoumarin-3-acetic acid, succinimidyl ester (AMCA, SE), are prepared. The degree of substitution achieved on the selected proteins (goat anti-mouse IgG (GAM), streptavidin (STR) and wheat germ agglutinin (WGA) is then determined.

A fresh solution of the desired protein is prepared that is 10 mg protein/mL in 0.1M sodium bicarbonate. The desired labeling reagent (Compound 2 or 7-amino-4-methylcoumarin-3-acetic acid, succinimidyl ester) is dissolved in DMF to give a concentration of 10 mg dye/mL. An amount of the labeling reagent in DMF sufficient to give the desired dye:protein ratio is slowly added to the protein solution with stirring. A molar ratio of 10 equivalents dye to equivalent of protein is typical, though the optimal amount varies with particular labeling reagent and protein being labeled. The reaction mixture is then incubated at room temperature for one hour. The dye-protein conjugate is separated from free unreacted reagent by gel filtration on a CELLUFINE GH-25 column equilibrated in PBS. The initial, protein-containing blue fluorescent band is collected from the column, and the degree of substitution is determined by measuring the absorbance of the conjugate at 346 nm, and calculating the degree of substitution using an extinction coefficient of 14,000 cm$^{-1}$M$^{-1}$ for AMCA and 20,000 cm$^{-1}$M$^{-1}$ for Compound 2).

Using the above method, conjugates of streptavidin (STR), wheat germ agglutinin (WGA) and goat anti-mouse (GAM) are prepared using both Compound 2 and 7-amino-4-methylcoumarin-3-acetic acid, succinimidyl ester. The resulting degree of substitution of the proteins is then compared as a function of dye:protein ratio:

| Protein | Dye:Protein Ratio | Fluorophores/Protein (mole/mole) | |
|---|---|---|---|
| | | AMCA SE | Compound 2 |
| STR | 3 | 1.6 | 2.1 |
| STR | 5 | 2.7 | 3.0 |
| STR | 10 | 5.5 | 5.8 |
| STR | 15 | 8.8 | 8.3 |
| STR | 20 | 11.7 | 11.7 |
| STR | 25 | 14.5 | 14.7 |
| WGA | 5 | 2.7 | 2.8 |
| WGA | 10 | 3.6 | 5.0 |
| WGA | 15 | 4.4 | 6.7 |
| GAM | 3 | 1.9 | 1.7 |
| GAM | 5 | 2.9 | 3.1 |
| GAM | 8 | 4.4 | 4.5 |
| GAM | 10 | 5.2 | 5.8 |

As shown above, the conjugates of the present invention exhibit a similar degree of dye incorporation into streptavidin and GAM, and even higher incorporation in WGA, at similar molar ratios of reactive dye to protein.

Example 23

Total fluorescence of selected dye-conjugates as a function of degree of substitution The total fluorescence of selected dye-conjugates of the present invention is plotted against the degree of substitution of the selected conjugates. Measured total fluorescence is a product of both the degree of substitution of the conjugate and the quantum yield of the bound fluorophore, and is compared to a common standard (in this case, 7-amino-4-methylcoumarin). The degree of substitution is determined as described earlier (Example 22). The resulting dependence of fluorescence on degree of substitution is shown for streptavidin and goat anti-mouse conjugates in FIGS. 2 and 3 respectively. As shown, as the degree of substitution increases, the total fluorescence increases. The dye-conjugates of Compound 2 exhibit a higher fluorescence output than do the dye-conjugates of AMCA.

Example 24

Preparation of a lectin conjugate of AMCA

Wheat germ agglutinin (WGA) is dissolved at 10 mg/mL in 0.1M sodium bicarbonate pH 8.3, containing N-acetylglucosamine at a reagent-to-protein ratio of 15. The addition of N-acetylglucosamine is necessary to protect the active site of the lectin from reacting with the dye during the conjugation reaction. Compound 2 and AMCA, SE are dissolved at 10 mg/mL in DMF and added to the WGA solutions at a dye-to-protein molar ratio of 5, 10 and 15 and the solutions are stirred for 1 hour at room temperature. Both series of reactions are terminated by the addition of an amount of hydroxylamine to obtain a final concentration of 0.1M, and the resulting conjugates are purified using size exclusion chromatography, as described in Example 22. Both dyes produce conjugates having the degrees of substitution presented in Example 22, and all the conjugates exhibit a similar activity for binding to Gram-positive bacteria, such as Bacillus and Staphylococcus (see Example 32).

Example 25

Preparation of a bacterial conjugate of Compound 2

Freshly cultured bacteria are washed with water, then boiled in water for 45 minutes. The heat-killed bacteria ($5 \times 10^8$/mL) are labeled with Compound 2 (30 µg/mL) in 0.15M bicarbonate buffer, pH 8.6 at room temperature for 60 minutes with constant stirring. The remaining free dye is removed by washing three times with phosphate buffered saline (PBS), pH 7.4. The resulting labeled bacteria exhibit blue fluorescence.

Example 26

Utility of goat anti-mouse conjugate of Compound 2

The efficacy of a goat anti-mouse (GAM) antibody conjugate of Compound 2 is tested in parallel to that of a GAM antibody conjugate of AMCA (both prepared as described in Example 22). The comparison is performed using a test to detect anti-nuclear antibodies commercially available from INOVA Diagnostics Inc. (San Diego, Calif.). The commercial assay consists of a series of fixed cells on slides, and an autoimmune serum against cell nuclei. The GAM conjugate of Compound 2 has a degree of substitution of 4.5 moles of dye per mole of protein, while the GAM conjugate of AMCA, SE has a degree of substitution of 4.4 dyes per mole. The cell nuclei are treated with either positive serum or negative serum (as a control), and are then developed using solutions of either GAM-AMCA or GAM-Compound 2 at a concentration of 1–5 mg/mL. The conjugates of Compound 2 yield brighter nuclear staining and lower fluorescence background than the conjugate prepared using AMCA (approximately 50% more fluorescent, as measured using a fluorescent microscope coupled to a Photometrics Star-1 cooled CCD camera for quantitative digital imaging).

Example 27

Comparison of staining of GEPA Cells using antibody conjugates of Compound 2

A suspension of GEPA cells (a B-cell lymphoma) is treated with a monoclonal antibody directed against the ICAM adhesion molecule that is expressed on the surface of this cell line. The cells are stained in parallel with GAM-Compound 2 (having a degree of substitution of 4.5) or GAM-AMCA (having a degree of substitution of 4.4). The cells are stained using 5 µg of the desired GAM conjugate per 500,000 GEPA cells in a volume of 200 µL of PBS-BSA. All incubations are performed on ice for 30 minutes, and the cells are washed twice with cold phosphate buffered saline (PBS), 1% BSA, between steps. The washed cells are then analyzed on a FACS Vantage flow cytometer. Typically GEPA cells stained with GAM-Compound 2 exhibit a higher fluorescence than the cells stained with GAM-AMCA. A GAM conjugate fluorescein was utilized as a control for the system. The ratio of fluorescence of stained cells to unstained cells for fluorescein is 15.3, for AMCA is 6.6 and for Compound 2 is 12.4, thus showing the greater brightness of the GAM-Compound 2 conjugate.

Example 28

Preparation of an aminodextran conjugate of Compound 2

A sample of aminodextran (50 mg) having an average molecular weight of 10,000 and derivatized with an average of 3.6 amino groups, is dissolved in 0.1M sodium bicarbonate to give a concentration of 10 mg/mL. A solution of Compound 2 in DMF having a concentration of 10 mg/mL is added to the dextran solution in an amount to give a dye/dextran ratio of 4. After stirring at room temperature, the conjugated dextran is purified by gel filtration using SEPHADEX G-15 resin in water. The dextran solution is lyophilized, and the degree of substitution of the dextran is determined as described in Example 22 for protein conjugates.

Example 29

Labeling actin in cells using a phalloidin conjugate of Compound 2

Mammalian cells are grown on coverslips according to standard tissue culture procedures. After two days in culture, the growth medium is removed and the cells are rinsed twice with warm Hanks Balanced Salt Solution (HBSS; 0.14 g/L $CaCl_2$, 0.40 g/L KCl, 0.06 g/L $KH_2PO_4$, 0.10 g/L $MgCl_2.6H_2O$, 0.10 g/L $MgSO_4.7H_2O$, 8.0 g/L NaCl, 0.35 g/L $NaHCO_3$, 0.48 g/L $Na_2HPO_4$, 1 g/L D-glucose). Cells are then fixed in 3.7% formaldehyde diluted into HBSS for 10 minutes at room temperature. Cells are rinsed in phosphate buffered saline (PBS; 0.20 g/L KCl, 0.20 g/L $KH_2PO_4$, 8 g/L NaCl, 1.15 g/L $Na_2HPO_4$), and permeabilized in ice cold acetone for 10 minutes. The cells are then rehydrated in PBS for 10 minutes, and stained with a 165 nM solution of a labeled phalloidin (as described in Example 22) in PBS. The stained cells are then rinsed twice with PBS, mounted in the mounting medium of choice, and viewed using a standard filter set used for AMCA conjugates (see next example) on a fluorescence microscope. The staining of F-actin filaments using the phalloidin conjugate is consistent with that of obtained using a longer wavelength dye-conjugate, such as a tetramethylrhodamine phalloidin conjugate, only exhibiting blue fluorescence.

Example 30

Labeling actin in cells using a phalloidin conjugate of Compound 2 in conjunction with a nucleic acid stain Cells are grown, fixed and permeabilized as described in Example 29. After a 10 minutes rehydration in PBS, cells are blocked in a solution of 1% bovine serum albumin/1% normal goat serum/0.1% TWEEN-20 in PBS for 30 minutes. The nuclei are stained for contrast with SYTOX Green nucleic acid stain (Molecular Probes, Inc., Eugene Oreg.), which only stains cells with compromised cellular membranes. After rinsing in PBS, cells are then incubated with a 165 nm solution of a labeled phalloidin (as described in Example 20) diluted in PBS for 30 minutes. Cells are rinsed a final time in PBS, mounted in the mounting medium of choice, and viewed through either a multi-band filter, or DAPI (ex. 330±30 nm, em.>400 nm) and a fluorescein filter with a standard fluorescence microscope. Simultaneous staining of both F-actin and nuclei is consistent with staining by the individual probes.

Example 31

Preparing a DNA hybridization probe using fluorescent nucleotide conjugates For each labeling reaction, a microfuge tube containing about 1 µg of a ~700 bp Hind III-Bgl II fragment of the *E. coli* lacZ structural gene is heated for about 10 minutes at 95° C. to fully separate the strands. The DNA is immediately cooled on ice, to prevent the strands from reannealing. To the DNA mixture on ice is added 2 µL of a 2 mg/mL mixture of random sequence hexanucleotides, in 0.5M Tris-HCl, pH 7.2, 0.1M MgCl$_2$, 1 mm dithiothreitol; 2 µL of a dNTP labeling mixture (1 mM dATP, 1 mM dGTP, 1 mM dCTP, 0.65 mM dTTP and 0.35 mM of a dUTP conjugate of Compound 2 (Example 18). Sterile distilled and deionized water is added to the samples to bring the total volume of each to 19 µL. A 1 µL volume of Klenow DNA polymerase (2 units/µL) is added carefully to the samples and they are mixed by pipetting up and down repeatedly. The samples are incubated for one hour at 37° C. The reaction is stopped by adding 2 µL of 0.2M EDTA, pH 8.0. The labeled DNA is precipitated by addition of 2.5 µL of 4M LiCl and 75 µL prechilled (-20° C.) 100% ethanol and mixing well. Precipitation is allowed to continue for 2 hours at -20° C. and the nucleic acid is then recovered by centrifugation at 5000 rpm in a microfuge. The pellet is washed briefly with cold 70% ethanol, then with cold 100% ethanol. The pellet is dried briefly and dissolved in 10 mM Tris-HCl, pH 8.0, 1 mM EDTA. A portion consisting of ¹⁄₁₀ to ½ of the sample is analyzed by gel electrophoresis on a 1% agarose minigel under standard conditions. The Compound 2-labeled dUTP (Compound 17) gives rise to clearly visible labeled DNA products that exhibit bright blue fluorescence when visualized using ultraviolet trans- or epi-illumination. The labeled DNA products are suitable for in situ hybridization experiments for the detection of RNA or DNA associated with the *E. coli* lacZ gene in cells or tissues.

Example 32

Use of a wheat germ agglutinin conjugate of Compound 2 to identify Gram positive bacteria A 2 mg/mL stock solution of a wheat germ agglutinin conjugate of AMCA (as prepared in Example 24) is prepared using 0.1M sodium bicarbonate at pH 8.3. A 100 µL aliquot of a bacterial suspension of either *Bacillus subtilis* or *Staphylococcus aureus* (approximately 5×10$^7$ cells) is centrifuged in a 0.2 µm-pore size spin filter at 2000 rpm for 1-2 minutes. The cells are then washed by pipetting up and down several times in 100 µL of a solution containing 0.25% bovine serum albumin and 0.15M NaCl. The cells are then recentrifuged as above, and resuspended in 100 µL of the BSA-saline solution. A 5.0 µL aliquot of the dye-WGA conjugate stock solution is added, and mixed well. The sample is then incubated for 5-15 minutes at room temperature. The stained sample is centrifuged at 2000 rpm for 1-2 minutes to remove the staining solution, and the bacteria are resuspended in 100 µL of the BSA-saline solution. Approximately 10 µL of the suspension is transferred to a slide, a coverslip is applied and sealed, and the sample is observed immediately using a fluorescence microscope. The Gram-positive bacteria exhibit blue fluorescence.

Example 33

Binding of opsonized labeled *E. coli* to the Fc receptor of neutrophils

Heat-killed bacteria are prepared and labeled with Compound 2 as described in Example 25. The labeled bacteria are then opsonized either with a 1:50 dilution of rabbit polyclonal anti-bacteria IgG, or with a 1:50 dilution of fresh human serum in PBS, (pH 7.4) at 4° C. for 30 minutes, then washed with PBS. The opsonized bacteria are incubated with human neutrophils at a ratio of 100:1 in PBS at 4° C. for 30 minutes, then at 37° C. for 30 minutes. Following washing with PBS, neutrophils are examined under a microscope to identify the phagocytosis of the labeled bacteria. Phagocytosis is quantitated as a phagocytic index (PI), the number of phagocytosed bacteria in 100 neutrophils. Alternatively, phagocytosis is assessed by flow cytometry using the fluorescence intensity of individual Compound 2 labeled bacteria as the reference to calculate the phagocytosis index.

Example 34

Labeling efficiency of a thiol-reactive sulfonated coumarin

A solution of Compound 5 dissolved at 10 mg/mL in DMF is added to a solution of β-galactosidase 10 mg/mL in 0.1M phosphate, 0.1M NaCl pH 7.5 at a molar dye-to-protein ratio of 20. The reaction mixture is allowed to stir for 2 hours at room temperature under an argon atmosphere. The availability of ten or more free thiol moieties on the protein results in a degree of substitution of 6.3 dyes per protein for Compound 5. The analogous labeling experiment performed with AMCA maleimide results in a DOS of 4.3 dyes per protein.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula

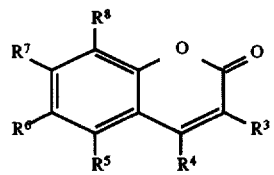

wherein
  $R^5$ is H;
  $R^6$ is H, methyl, halogen, or SO$_3$X;
  $R^7$ is NR$^1$R$^2$; wherein
    $R^1$ and $R^2$ are independently H, C$_1$-C$_{18}$ alkyl, C$_6$-C$_{18}$ aryl, C$_1$-C$_{18}$ alkanoyl, C$_7$-C$_{18}$ arylalkanoyl;
    or $R^1$ in combination with $R^2$ forms a saturated 5- or 6-membered heterocycle that is a piperidine, a morpholine, a pyrrolidine or a piperazine;

37 or R² is H and R¹ is a radical formed by a removal of the hydroxyl group from the carboxylic acid of an amino acid or from the carboxylic acid of the carboxy-terminal amino acid of a linear peptide consisting of 2–6 amino acids;

or R¹ is a 2-nitrobenzyloxycarbonyl of the formula

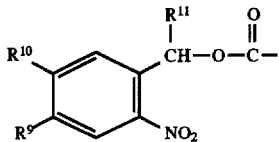

wherein

R⁹ and R¹⁰ are H, $C_1$–$C_6$ alkoxy, or R⁹ and R¹⁰ taken in combination are —O—CH₂—O—; and R¹¹ is H, CH₃, a carboxylic acid or a biologically compatible salt of a carboxylic acid;

or R⁷ is a nitrogen atom that is linked by a single or double covalent bond to the anomeric carbon of a mono- or polysaccharide and formally replaces the anomeric oxygen atom of the mono- or polysaccharide;

R⁸ is H, halogen or SO₃X;

X is H, or a biologically compatible cation;

R³ is H, SO₃X, halogen, CN, NO₂, or —L—$R_X$ or —L—$S_C$;

R⁴ is H, CN, $C_1$–$C_{18}$ alkyl, $C_1$–$C_{18}$ perfluoroalkyl, CH₂SO₃X; or —L—$R_X$ or —L—$S_C$; wherein each L is a single covalent bond, or L is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds;

$R_X$ is a reactive group; and $S_C$ is a conjugated substance;

provided that at least one of R³, R⁶ or R⁸ is SO₃X.

2. A compound, as claimed in claim 1, wherein one of R³ and R⁴ is —L—$R_X$.

3. A compound, as claimed in claim 2, wherein $R_X$ is an acrylamide, a carboxylic acid, an activated ester of a carboxylic acid, a hydroxy, an aldehyde, an alkyl halide, a sulfonate, an amine, an anhydride, an aniline, an aryl halide, an azide, an aziridine, a boronate, a carbodiimide, an epoxide, a glycol, a haloacetamide, a halotriazine, a hydrazine, a hydroxylamine, an isothiocyanate, a ketone, a maleimide, a sulfonyl halide, or a thiol group.

4. A compound, as claimed in claim 1, wherein $R_X$ is a carboxylic acid, an activated ester of a carboxylic acid, an alcohol, an aldehyde, an alkyl halide, an amine, a haloacetamide, a halotriazine, a hydrazine, an isothiocyanate, a maleimide or a thiol.

5. A compound, as claimed in claim 2, wherein R³ is —L—$R_X$ and $R_X$ is a succinimidyl ester.

6. A compound, as claimed in claim 1, wherein R⁴ is sulfomethyl, halomethyl, $C_1$–$C_{18}$ alkyl or $C_1$–$C_{18}$ perfluoroalkyl.

7. A compound, as claimed in claim 1, wherein one of R³ and R⁴ is —L—$S_C$.

8. A compound, as claimed in claim 7, wherein $S_C$ is an amino acid, a tyramine, a peptide, a protein, a monosaccharide, a polysaccharide, an ion-complexing moiety, a nucleoside, a nucleotide, an oligonucleotide, a nucleic acid, a hapten, a drug, a lipid, a phospholipid, a lipoprotein, a lipopolysaccharide, a liposome, a lipophilic polymer, a polymeric microparticle, an animal cell, a plant cell, a bacterium, a yeast, or a virus.

9. A compound, as claimed in claim 8, wherein $S_C$ is an amino acid, a peptide, a protein, a nucleotide, an oligonucleotide, a nucleic acid, a monosaccharide, a polysaccharide, or a drug.

10. A compound, as claimed in claim 9, wherein $S_C$ is a peptide or a protein.

11. A compound, as claimed in claim 7, wherein $S_C$ is further substituted by one or more additional dye compounds, which may be the same or different.

12. A compound, as claimed in claim 1, wherein R⁷ is NR¹R² and R¹ and R² are independently H or $C_1$–$C_{18}$ alkyl.

13. A compound, as claimed in claim 1, wherein R⁷ is NR¹R², where R² is H and R¹ is a radical formed by a removal of the hydroxyl group from the carboxylic acid of an amino acid or from the carboxylic acid of the carboxy-terminal amino acid of a linear peptide consisting of 2–6 amino acids.

14. A compound, as claimed in claim 1, wherein R⁷ is NR1R², where R² is H and R¹ is a 2-nitrobenzyloxycarbonyl of the formula

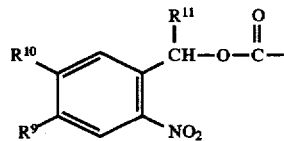

wherein

R⁹ and R¹⁰ are H, $C_1$–$C_6$ alkoxy, or R⁹ and R¹⁰ taken in combination are —O—CH₂—O—; and R¹¹ is H, CH₃, a carboxylic acid or a biologically compatible salt of a carboxylic acid.

15. A compound, as claimed in claim 1, wherein R⁷ is a nitrogen atom that is linked by a single or double covalent bond to the anomeric carbon of a mono- or polysaccharide and formally replaces the anomeric oxygen atom of the mono- or polysaccharide.

16. A compound, as claimed in claim 1, wherein

R³ is H, —L—$R_X$, or —L—$S_C$;

R⁴ is CH₃, —L—$R_X$ or —L—$S_C$

R⁷ is NH₂; and

R⁸ is H;

provided that at least one of R³, R⁶ and R⁸ is SO₃X.

17. A method of detecting a complementary member of a specific binding pair in a sample, comprising:

a) adding to said sample a dye-conjugate of a first member of a specific binding pair for which there is a complementary member, where said first member of a specific binding pair is attached to one or more dye molecules, which may be the same or different, having the formula

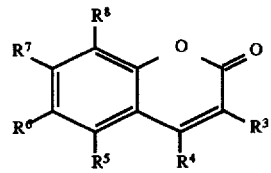

wherein

R⁵ is H;

R⁶ is H, methyl, halogen, or SO₃X;

R⁷ is NR¹R²; wherein

R¹ and R² are independently H, $C_1$–$C_{18}$ alkyl; or R¹ in combination with R² forms a saturated 5- or 6-membered heterocycle that is a piperidine, a morpholine, a pyrrolidine or a piperazine;

or $R^1$ is a 2-nitrobenzyloxycarbonyl of the formula

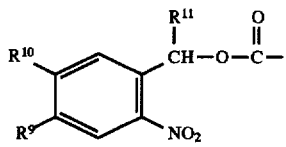

wherein $R^9$ and $R^{10}$ are H, $C_1$–$C_6$ alkoxy, or $R^9$ and $R^{10}$ taken in combination are —O—$CH_2$—O—; and $R^{11}$ is H, $CH_3$, a carboxylic acid or a biologically compatible salt of a carboxylic acid;

$R^8$ is H, halogen or $SO_3X$;

X is H, or a biologically compatible cation;

$R^3$ is H, $SO_3X$, halogen, CN, $NO_2$, or —L—$S_C$;

$R^4$ is H, CN, $C_1$–$C_{18}$ alkyl, $C_1$–$C_{18}$ perfluoroalkyl, $CH_2SO_3X$; or —L—$S_C$; wherein each L is a single covalent bond, or L is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds; and $S_C$ is a conjugated substance that is said first member of a specific binding pair;

provided that at least one of $R^3$, $R^6$ or $R^8$ is $SO_3X$; and provided that one of $R^3$ and $R^4$ is —L—$S_C$;

b) allowing sufficient time for the dye-conjugate to form a complex with the complementary member, said complex exhibiting a detectable optical response; and c) detecting said complex to locate the complementary member.

18. A method, as claimed in claim 17, wherein the first member of the specific binding pair is a peptide, a protein, a nucleotide, an oligonucleotide, a nucleic acid polymer, a drug, a toxin, or a polysaccharide.

19. A method, as claimed in claim 17, wherein the optical response is a fluorescence response.

20. A method, as claimed in claim 17, wherein the first member of the specific binding pair is an antibody, an antibody fragment, avidin, streptavidin, or a conjugate of an antibody, an antibody fragment, avidin, or streptavidin and the complementary member is a hapten having a molecular weight less than 1,000, an antigen or a biotin.

21. A method, as claimed in claim 17, wherein the complementary member is present in a cell, bacteria, virus, yeast cell or is immobilized on a polymer, polymeric membrane or polymeric particle.

22. A method, as claimed in claim 19, further comprising distinguishing said fluorescence response from that of a second fluorophore having detectably different optical properties.

23. A method of staining a sample, comprising:

a) adding to said sample a compound of the formula

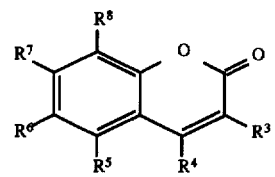

wherein $R^5$ is H;

$R^6$ is H, methyl, halogen, or $SO_3X$;

$R^7$ is $NR^1R^2$; wherein $R^1$ and $R^2$ are independently H, $C_1$–$C_{18}$ alkyl; or $R^1$ in combination with $R^2$ forms a saturated 5- or 6-membered heterocycle that is a piperidine, a morpholine, a pyrrolidine or a piperazine;

or $R^2$ is H and $R^1$ is a radical formed by a removal of the hydroxyl group from the carboxylic acid of an amino acid or from the carboxylic acid of the carboxy-terminal amino acid of a linear peptide consisting of 2–6 amino acids;

or $R^1$ is a 2-nitrobenzyloxycarbonyl of the formula

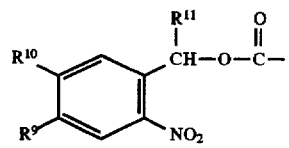

wherein $R^9$ and $R^{10}$ are H, $C_1$–$C_6$ alkoxy, or $R^9$ and $R^{10}$ taken in combination are —O—$CH_2$—O—; and $R^{11}$ is H, $CH_3$, a carboxylic acid or a biologically compatible salt of a carboxylic acid;

$R^8$ is H, halogen or $SO_3X$;

X is H, or a biologically compatible cation;

$R^3$ is H, $SO_3X$, halogen, CN, $NO_2$, or —L—$S_C$;

$R^4$ is H, CN, $C_1$–$C_{18}$ alkyl, $C_1$–$C_{18}$ perfluoroalkyl, $CH_2SO_3X$; or —L—$S_C$; wherein each L is a single covalent bond, or L is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds; and $S_C$ is a conjugated substance;

provided that at least one of $R^3$, $R^6$ or $R^8$ is $SO_3X$;

in an amount sufficient to produce an optical response when said sample is illuminated at an appropriate wavelength.

24. A method, as claimed in claim 23, wherein said optical response is a fluorescence response.

25. A method, as claimed in claim 23, wherein said sample comprises cells.

26. A method, as claimed in claim 25, further comprising observing said cells using flow cytometry.

27. A method, as claimed in claim 24, further comprising distinguishing the fluorescence response from that of a second fluorophore having detectably different optical properties.

* * * * *

UNITED STATES PATENT AND TRADEMARK OFFICE
CERTIFICATE OF CORRECTION

PATENT NO. : 5,696,157
DATED : Dec. 9, 1997
INVENTOR(S) : Wang et al

It is certified that error appears in the above-indentified patent and that said Letters Patent is hereby corrected as shown below:

At column 14, line 48, "iipids" should be --lipids--.

At column 15, line 19, "histories" should be --histones--.

At column 19, line 20, "$R^I$ is H" should be --$R^1$ is H--.

At column 20, line 65, "clearable" should be --cleavable--.

At column 38, claim 16, line 44, "$R^8$ is H;" should be --$R^5$ is H;--.

Signed and Sealed this

Thirty-first Day of October, 2000

Attest:

Q. TODD DICKINSON

*Attesting Officer*                *Director of Patents and Trademarks*